(12) United States Patent
Ryan

(10) Patent No.: US 9,487,819 B2
(45) Date of Patent: Nov. 8, 2016

(54) QUANTITATIVE GENETICALLY ENCODED OPTICAL REPORTER CONSTRUCT

(75) Inventor: Timothy A. Ryan, New York, NY (US)

(73) Assignee: Cornell University, Ithaca, NY (US)

(*) Notice: Subject to any disclaimer, the term of this patent is extended or adjusted under 35 U.S.C. 154(b) by 310 days.

(21) Appl. No.: 13/445,534

(22) Filed: Apr. 12, 2012

(65) Prior Publication Data
US 2014/0017696 A1 Jan. 16, 2014

Related U.S. Application Data

(63) Continuation-in-part of application No. PCT/US2010/052787, filed on Oct. 15, 2010.

(60) Provisional application No. 61/252,262, filed on Oct. 16, 2009.

(51) Int. Cl.
C12Q 1/66 (2006.01)
C12N 15/10 (2006.01)
C12Q 1/00 (2006.01)
G01N 33/50 (2006.01)

(52) U.S. Cl.
CPC ............ *C12Q 1/66* (2013.01); *C12N 15/1086* (2013.01); *C12Q 1/008* (2013.01); *G01N 33/5035* (2013.01)

(58) Field of Classification Search
None
See application file for complete search history.

(56) References Cited

U.S. PATENT DOCUMENTS 7,601,517 B2 10/2009 Gambhir et al.
2009/0148449 A1 6/2009 Deweers et al.

FOREIGN PATENT DOCUMENTS

WO WO2005123918 6/2005

OTHER PUBLICATIONS

Accession DD332917. Oct. 23, 2006.*
Accession AY678264. Dec. 17, 2004.*
Accession X06177. Sep. 12, 1993.*
Granseth et al. Neuron. Sep. 21, 2006;51(6):773-86.*
Validation Report for Sequence Listing. Feb. 22, 2016.*
PCT Search Report and Written Opinion. PCT/US2010/52787. Jan. 18, 2011.
Branchini et al., Thermostable red and green light-producing firefly luciferase mutants for bioluminescent reporter applications, Analytical Biochemistry, vol. 361, pp. 253-262, 2007.
Fujii et al., Increase in bioluminescence intensity of firefly luciferase using genetic modification. Analytical Biochemistry, vol. 366, pp. 131-136, 2007.
Sasaki et al. Improvement or DNA vaccine immunogenicity by a dual antigen expression system. Biochem Biophys Res Commun. vol. 315, No. 1; pp. 38-43, 2004. abstract only.

* cited by examiner

*Primary Examiner* — Christian Fronda
(74) *Attorney, Agent, or Firm* — Springut Law PC; Franklin S. Abrams

(57) ABSTRACT

An isolated nucleic acid reporter construct, the protein for which it encodes and methods for its use for the in vivo or in vitro measurement of the concentration of a specific biologically important molecule in a subcellular compartment or locale are provided. Certain constructs described are useful in measuring the local concentration of ATP at synapses.

17 Claims, 17 Drawing Sheets

Fig. 1: Design, optimization and calibration of Syn-ATP

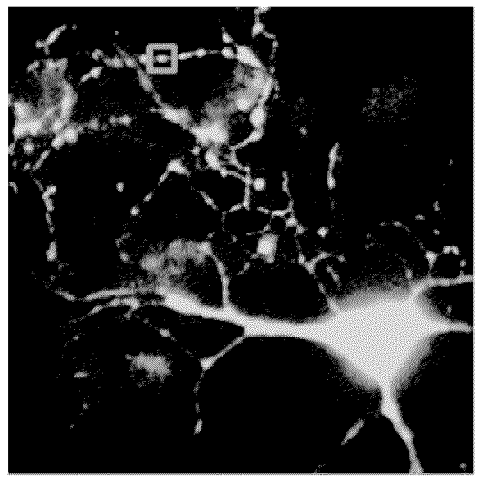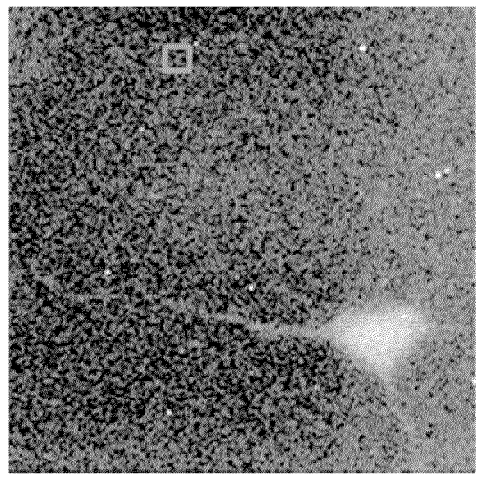
Fig. 4

SEQUENCE LISTING

<160> NUMBER OF SEQ ID NOS: 7

<210> SEQ ID NO 1
<211> LENGTH: 1653
<212> TYPE: DNA
<213> ORGANISM: Photonis pyralis

<400> SEQUENCE: 1

```
atggaagacg ccaaaaacat aaagaaaggc ccggcgccat tctatccgct ggaagatgga    60
accgctggag agcaactgca taaggctatg aagagatacg ccctggttcc tggaacaatt   120
gcttttacag atgcacatat cgaggtggac atcacttacg ctgagtactt cgaaatgtcc   180
gttcggttgg cagaagctat gaacgatat gggctgaata caatcacag aatcgtcgta    240 tgcagtgaaa actctcttca attctttatg ccggtgttgg gcgcgttatt tatcggagtt   300
gcagttgcgc ccgcgaacga catttataat gaacgtgaat tgctcaacag tatgggcatt   360
tcgcagccta ccgtggtgtt cgtttccaaa aagggggttgc aaaaaatttt gaacgtgcaa   420
```

```
aaaaagctcc caatcatcca aaaaattatt atcatggatt ctaaaacgga ttaccaggga      480
tttcagtcga tgtacacgtt cgtcacatct catctacctc ccggttttaa tgaatacgat      540
tttgtgccag agtccttcga tagggacaag acaattgcac tgatcatgaa ctcctctgga      600
tctactggtc tgcctaaagg tgtcgctctg cctcatagaa ctgcctgcgt gagattctcg      660
catgccagag atcctatttt tggcaatcaa atcattccgg atactgcgat tttaagtgtt      720
gttccattcc atcacggttt tggaatgttt actacactcg atatttgat atgtggattt       780 cgagtcgtct taatgtatag atttgaagaa gagctgtttc tgaggagcct tcaggattac      840
aagattcaaa gtgcgctgct ggtgccaacc ctattctcct tcttcgccaa aagcactctg      900
attgacaaat acgatttatc taatttacac gaaattgctt ctggtggcgc tcccctctct      960
aaggaagtcg gggaagcggt tgccaagagg ttccatctgc caggtatcag gcaaggatat     1020
gggctcactg agactacatc agctattctg attacacccg aggggatga taaaccgggc      1080 gcggtcggta agttgttcc attttttgaa gcgaaggttg tggatctgga taccgggaaa      1140
acgctgggcg ttaatcaaag aggcgaactg tgtgtgagag gtcctatgat tatgtccggt      1200
tatgtaaaca atccggaagc gaccaacgcc ttgattgaca aggatggatg gctacattct      1260
ggagacatag cttactggga cgaagacgaa cacttcttca tcgttgaccg cctgaagtct      1320
ctgattaagt acaaaggcta tcaggtggct cccgctgaat tggaatccat cttgctccaa      1380 cacccaaca tcttcgacgc agtgtcgca ggtcttcccg acgatgacgc cggtgaactt       1440
cccgccgccg ttgttgtttt ggagcacgga agacgatga cggaaaaaga gatcgtggat      1500
tacgtcgcca gtcaagtaac aaccgcgaaa agttgcgcg gaggagttgt gtttgtggac      1560
gaagtaccga aaggtcttac cggaaaactc gacgcaagaa aaatcagaga gatcctcata      1620
aaggccaaga agggcggaaa gatcgccgtg taa                                   1653

<210> SEQ ID NO 2
<211> LENGTH: 708
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 2
atggtgagca agggcgagga ggataacatg gccatcatca aggagttcat gcgcttcaag       60
gtgcacatgg agggctccgt gaacggccac gagttcgaga tcgagggcga gggcgagggc      120
cgcccctacg agggcaccca gaccgccaag ctgaaggtga ccaagggtgg cccccctgccc     180 ttcgcctggg acatcctgtc ccctcagttc atgtacggct ccaaggccta cgtgaagcac      240
cccgccgaca tccccgacta cttgaagctg tccttccccg agggcttcaa gtgggagcgc      300
gtgatgaact tcgaggacgg cggcgtggtg accgtgaccc aggactcctc cctgcaggac      360
ggcgagttca tctacaaggt gaagctgcgc ggcaccaact cccctccga cggcccgta       420 atgcagaaga agaccatggg ctgggaggcc tcctccgagc ggatgtaccc cgaggacggc      480
gccctgaagg gcgagatcaa gcagaggctg aagctgaagg acggcggcca ctacgacgct      540
gaggtcaaga ccacctacaa ggccaagaag cccgtgcagc tgcccggcgc ctacaacgtc      600
aacatcaagt tggacatcac ctcccacaac gaggactaca ccatcgtgga acagtacgaa      660
cgcgccgagg gccgccactc caccggcggc atggacgagc tgtacaag                   708

<210> SEQ ID NO 3
```

```
<211> LENGTH: 921
<212> TYPE: DNA
<213> ORGANISM: Homo sapiens

<400> SEQUENCE: 3
atggacgtgg tgaatcagct ggtggctggg ggtcagttcc gggtggtcaa ggagcccctt      60
ggcttcgtga aggtgctgca gtgggtcttt gccatcttcg cctttgctac gtgtggcagc     120
tacaccgggg agcttcggct gagcgtggag tgtgccaaca agacggagag tgccctcaac     180
atcgaagttg aattcgagta ccccttcagg ctgcaccaag tgtactttga tgcaccctcc     240
tgcgtcaaag ggggcactac caagatcttc ctggttgggg actactcctc gtcggctgaa     300
ttctttgtca ccgtggctgt gtttgccttc ctctactcca tgggggccct ggccacctac     360
atcttcctgc agaacaagta ccgagagaac aacaaagggc ctatgatgga ctttctggct     420
acagccgtgt tcgctttcat gtggctagtt agttcatcag cctgggccaa aggcctgtcc     480
gatgtgaaga tggccacgga cccagagaac attatcaagg agatgccatg tgccgccag      540 acagggaaca catgcaagga actgagggac cctgtgactt caggactcaa cacctcagtg     600
gtgtttggct tcctgaacct ggtgctctgg gttggcaact tatggttcgt gttcaaggag     660
acaggctggg cagccccatt catgcgcgca cctccaggcg ccccggaaaa gcaaccagca     720
cctggcgatg cctacggcga tgcgggctac gggcagggcc ccggaggcta tgggccccaa     780
gactcctacg ggcctcaggg tggttatcaa cccgattacg ggcagccagc cagcggtggc     840
ggtggctacg ggcctcaggg cgactatggg cagcaaggct atggccaaca gggtgcgccc     900
acctccttct ccaatcagat g                                               921

<210> SEQ ID NO 4
<211> LENGTH: 3486
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 4
ggagacccaa gcttggtacc gagctcggat ccgcggccgc tctagcgcta ccggactcag      60
atctcgagct caatcctgaa ttcatggacg tggtgaatca gctggtggct gggggtcagt     120
tccgggtggt caaggagccc cttggcttcg tgaaggtgct gcagtgggtc tttgccatct     180
tcgcctttgc tacgtgtggc agctacaccg ggagcttcg gctgagcgtg gagtgtgcca      240
acaagacgga gagtgccctc aacatcgaag ttgaattcga gtaccccttc aggctgcacc     300
aagtgtactt tgatgcaccc tcctgcgtca aggggggcac taccaagatc ttcctggttg     360
gggactactc ctcgtcggct gaattctttg tcaccgtggc tgtgtttgcc ttcctctact     420
ccatgggggc cctggccacc tacatcttcc tgcagaacaa gtaccgagag aacaacaaag     480
ggcctatgat ggactttctg gctacagccg tgttcgcttt catgtggcta gttagttcat     540
cagcctgggc caaaggcctg tccgatgtga agatggccac ggacccagag aacattatca     600
aggagatgcc catgtgccgc cagacaggga cacatgcaa ggaactgagg gaccctgtga      660
cttcaggact caacacctca gtggtgtttg gcttcctgaa cctggtgctc tgggttggca     720
acttatggtt cgtgttcaag gagacaggct gggcagcccc attcatgcgc gcacctccag     780
gcgcccggga aaagcaacca gcacctggcg atgcctacgg cgatgcgggc tacgggcagg     840
gccccggagg ctatgggccc caagactcct acgggcctca gggtggttat caacccgatt     900
```

```
acgggcagcc agccagcggt ggcggtggct acgggcctca gggcgactat gggcagcaag      960
gctatggcca acagggtgcg cccacctcct tctccaatca gatgggatcc actagtaacg     1020
gccgccagtg tgctggaatt ctgcagatat cgatggtgag caagggcgag gaggataaca     1080
tggccatcat caaggagttc atgcgcttca aggtgcacat ggagggctcc gtgaacggcc     1140
acgagttcga gatcgagggc gagggcgagg gccgccccta cgagggcacc cagaccgcca     1200
agctgaaggt gaccaagggt ggccccctgc ccttcgcctg gacatcctg tcccctcagt      1260 tcatgtacgg ctccaaggcc tacgtgaagc accccgccga catccccgac tacttgaagc     1320
tgtccttccc cgagggcttc aagtgggagc gcgtgatgaa cttcgaggac ggcggcgtgg     1380
tgaccgtgac ccaggactcc tccctgcagg acggcgagtt catctacaag gtgaagctgc     1440
gcggcaccaa cttcccctcc gacggccccg taatgcagaa gaagaccatg ggctgggagg     1500
cctcctccga gcggatgtac cccgaggacg cgcgcctgaa gggcgagatc aagcagaggc     1560
tgaagctgaa ggacggcggc cactacgacg ctgaggtcaa gaccacctac aaggccaaga     1620
agcccgtgca gctgccggc gcctacaacg tcaacatcaa gttggacatc acctcccaca      1680
acgaggacta caccatcgtg aacagtacg aacgcgccga gggccgccac tccaccggcg      1740
gcatggacga gctgtacaag ggaccggtgc tagcggtacc gagctcggat ccactagtcc     1800
agtgtggtgg aattgccctt atggaagacg ccaaaaacat aaagaaaggc ccggcgccat     1860
tctatccgct ggaagatgga accgctggag agcaactgca taaggctatg aagagatacg     1920
ccctggttcc tggaacaatt gcttttacag atgcacatat cgaggtggac atcacttacg     1980
ctgagtactt cgaaatgtcc gttcggttgg cagaagctat gaaacgatat gggctgaata     2040
caaatcacag aatcgtcgta tgcagtgaaa actctcttca attctttatg ccggtgttgg     2100
gcgcgttatt tatcggagtt gcagttgcgc ccgcgaacga catttataat gaacgtgaat     2160
tgctcaacag tatgggcatt tcgcagccta ccgtggtgtt cgtttccaaa aagggggttgc    2220 aaaaaatttt gaacgtgcaa aaaaagctcc caatcatcca aaaaattatt atcatggatt     2280
ctaaaacgga ttaccaggga tttcagtcga tgtacacgtt cgtcacatct catctacctc     2340
ccggttttaa tgaatacgat tttgtgccag agtccttcga tagggacaag acaattgcac     2400
tgatcatgaa ctcctctgga tctactggtc tgcctaaagg tgtcgctctg cctcatagaa     2460
ctgcctgcgt gagattctcg catgccagag atcctatttt tggcaatcaa atcattccgg     2520
atactgcgat tttaagtgtt gttccattcc atcacggttt tggaatgttt actacactcg     2580
gatatttgat atgtggattt cgagtcgtct taatgtatag atttgaagaa gagctgtttc     2640
tgaggagcct tcaggattac aagattcaaa gtgcgctgct ggtgccaacc ctattctcct     2700
tcttcgccaa aagcactctg attgacaaat acgatttatc taatttacac gaaattgctt     2760
ctggtggcgc tccctctct aaggaagtcg gggaagcggt tgccaagagg ttccatctgc      2820
caggtatcag gcaaggatat gggctcactg agactacatc agctattctg attacacccg     2880
agggggatga taaaccgggc gcggtcgta agttgttcc attttttgaa gcgaaggttg       2940
tggatctgga taccgggaaa acgctgggcg ttaatcaaag aggcgaactg tgtgtgagag     3000
gtcctatgat tatgtccggt tatgtaaaca atccggaagc gaccaacgcc ttgattgaca     3060
aggatggatg gctacattct ggagacatag cttactggga cgaagacgaa cacttcttca     3120
tcgttgaccg cctgaagtct ctgattaagt acaaaggcta tcaggtggct cccgctgaat     3180
tggaatccat cttgctccaa caccccaaca tcttcgacgc aggtgtcgca ggtcttcccg     3240
acgatgacgc cggtgaactt cccgccgccg ttgttgtttt ggagcacgga aagacgatga     3300
```

```
cggaaaaaga gatcgtggat tacgtcgcca gtcaagtaac aaccgcgaaa aagttgcgcg    3360
gaggagttgt gtttgtggac gaagtaccga aaggtcttac cggaaaactc gacgcaagaa    3420
aaatcagaga gatcctcata aaggccaaga agggcggaaa gatcgccgtg taagcggccg    3480
ctcgag                                                              3486
```

<210> SEQ ID NO 5
<211> LENGTH: 1114
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 5

```
Met Asp Val Val Asn Gln Leu Val Ala Gly Gly Gln Phe Arg Val Val
 1               5                  10                  15

Lys Glu Pro Leu Gly Phe Val Lys Val Leu Gln Trp Val Phe Ala Ile
                20                  25                  30

Phe Ala Phe Ala Thr Cys Gly Ser Tyr Thr Gly Glu Leu Arg Leu Ser
            35                  40                  45

Val Glu Cys Ala Asn Lys Thr Glu Ser Ala Leu Asn Ile Glu Val Glu
        50                  55                  60

Phe Glu Tyr Pro Phe Arg Leu His Gln Val Tyr Phe Asp Ala Pro Ser
65                  70                  75                  80

Cys Val Lys Gly Gly Thr Thr Lys Ile Phe Leu Val Gly Asp Tyr Ser
                85                  90                  95

Ser Ser Ala Glu Phe Phe Val Thr Val Ala Val Phe Ala Phe Leu Tyr
            100                 105                 110

Ser Met Gly Ala Leu Ala Thr Tyr Ile Phe Leu Gln Asn Lys Tyr Arg
        115                 120                 125

Glu Asn Asn Lys Gly Pro Met Met Asp Phe Leu Ala Thr Ala Val Phe
    130                 135                 140

Ala Phe Met Trp Leu Val Ser Ser Ser Ala Trp Ala Lys Gly Leu Ser
145                 150                 155                 160

Asp Val Lys Met Ala Thr Asp Pro Glu Asn Ile Ile Lys Glu Met Pro
                165                 170                 175

Met Cys Arg Gln Thr Gly Asn Thr Cys Lys Glu Leu Arg Asp Pro Val
            180                 185                 190

Thr Ser Gly Leu Asn Thr Ser Val Val Phe Gly Phe Leu Asn Leu Val
        195                 200                 205

Leu Trp Val Gly Asn Leu Trp Phe Val Phe Lys Glu Thr Gly Trp Ala
    210                 215                 220

Ala Pro Phe Met Arg Ala Pro Pro Gly Ala Pro Glu Lys Gln Pro Ala
225                 230                 235                 240

Pro Gly Asp Ala Tyr Gly Asp Ala Gly Tyr Gly Gln Gly Pro Gly Gly
                245                 250                 255

Tyr Gly Pro Gln Asp Ser Tyr Gly Pro Gln Gly Gly Tyr Gln Pro Asp
            260                 265                 270

Tyr Gly Gln Pro Ala Ser Gly Gly Gly Tyr Gly Pro Gln Gly Asp
        275                 280                 285

Tyr Gly Gln Gln Gly Tyr Gly Gln Gly Ala Pro Thr Ser Phe Ser
    290                 295                 300

Asn Gln Met Gly Ser Thr Ser Asn Gly Arg Gln Cys Ala Gly Ile Leu
305                 310                 315                 320
```

```
Gln Ile Ser Met Val Ser Lys Gly Glu Glu Asp Asn Met Ala Ile Ile
                325                 330                 335

Lys Glu Phe Met Arg Phe Lys Val His Met Glu Gly Ser Val Asn Gly
            340                 345                 350

His Glu Phe Glu Ile Glu Gly Glu Gly Arg Pro Tyr Glu Gly
        355                 360                 365

Thr Gln Thr Ala Lys Leu Lys Val Thr Lys Gly Gly Pro Leu Pro Phe
    370                 375                 380

Ala Trp Asp Ile Leu Ser Pro Gln Phe Met Tyr Gly Ser Lys Ala Tyr
385                 390                 395                 400

Val Lys His Pro Ala Asp Ile Pro Asp Tyr Leu Lys Leu Ser Phe Pro
                405                 410                 415

Glu Gly Phe Lys Trp Glu Arg Val Met Asn Phe Glu Asp Gly Gly Val
            420                 425                 430

Val Thr Val Thr Gln Asp Ser Ser Leu Gln Asp Gly Glu Phe Ile Tyr
        435                 440                 445

Lys Val Lys Leu Arg Gly Thr Asn Phe Pro Ser Asp Gly Pro Val Met
    450                 455                 460

Gln Lys Lys Thr Met Gly Trp Glu Ala Ser Ser Glu Arg Met Tyr Pro
465                 470                 475                 480

Glu Asp Gly Ala Leu Lys Gly Glu Ile Lys Gln Arg Leu Lys Leu Lys
                485                 490                 495

Asp Gly Gly His Tyr Asp Ala Glu Val Lys Thr Thr Tyr Lys Ala Lys
            500                 505                 510

Lys Pro Val Gln Leu Pro Gly Ala Tyr Asn Val Asn Ile Lys Leu Asp
        515                 520                 525

Ile Thr Ser His Asn Glu Asp Tyr Thr Ile Val Glu Gln Tyr Glu Arg
    530                 535                 540

Ala Glu Gly Arg His Ser Thr Gly Gly Met Asp Glu Leu Tyr Lys Gly
545                 550                 555                 560

Pro Val Leu Ala Met Glu Asp Ala Lys Asn Ile Lys Lys Gly Pro Ala
                565                 570                 575

Pro Phe Tyr Pro Leu Glu Asp Gly Thr Ala Gly Glu Gln Leu His Lys
            580                 585                 590

Ala Met Lys Arg Tyr Ala Leu Val Pro Gly Thr Ile Ala Phe Thr Asp
        595                 600                 605

Ala His Ile Glu Val Asp Ile Thr Tyr Ala Glu Tyr Phe Glu Met Ser
    610                 615                 620

Val Arg Leu Ala Glu Ala Met Lys Arg Tyr Gly Leu Asn Thr Asn His
625                 630                 635                 640

Arg Ile Val Val Cys Ser Glu Asn Ser Leu Gln Phe Phe Met Pro Val
                645                 650                 655

Leu Gly Ala Leu Phe Ile Gly Val Ala Val Ala Pro Ala Asn Asp Ile
            660                 665                 670

Tyr Asn Glu Arg Glu Leu Leu Asn Ser Met Gly Ile Ser Gln Pro Thr
        675                 680                 685

Val Val Phe Val Ser Lys Lys Gly Leu Gln Lys Ile Leu Asn Val Gln
    690                 695                 700

Lys Lys Leu Pro Ile Ile Gln Lys Ile Ile Met Asp Ser Lys Thr
705                 710                 715                 720

Asp Tyr Gln Gly Phe Gln Ser Met Tyr Thr Phe Val Thr Ser His Leu
                725                 730                 735
```

```
Pro Pro Gly Phe Asn Glu Tyr Asp Phe Val Pro Glu Ser Phe Asp Arg
            740                 745                 750

Asp Lys Thr Ile Ala Leu Ile Met Asn Ser Ser Gly Ser Thr Gly Leu
        755                 760                 765

Pro Lys Gly Val Ala Leu Pro His Arg Thr Ala Cys Val Arg Phe Ser
    770                 775                 780

His Ala Arg Asp Pro Ile Phe Gly Asn Gln Ile Ile Pro Asp Thr Ala
785                 790                 795                 800

Ile Leu Ser Val Val Pro Phe His His Gly Phe Gly Met Phe Thr Thr
                805                 810                 815

Leu Gly Tyr Leu Ile Cys Gly Phe Arg Val Val Leu Met Tyr Arg Phe
            820                 825                 830

Glu Glu Glu Leu Phe Leu Arg Ser Leu Gln Asp Tyr Lys Ile Gln Ser
        835                 840                 845

Ala Leu Leu Val Pro Thr Leu Phe Ser Phe Phe Ala Lys Ser Thr Leu
    850                 855                 860

Ile Asp Lys Tyr Asp Leu Ser Asn Leu His Glu Ile Ala Ser Gly Gly
865                 870                 875                 880

Ala Pro Leu Ser Lys Glu Val Gly Glu Ala Val Ala Lys Arg Phe His
                885                 890                 895

Leu Pro Gly Ile Arg Gln Gly Tyr Gly Leu Thr Glu Thr Thr Ser Ala
            900                 905                 910

Ile Leu Ile Thr Pro Glu Gly Asp Lys Pro Gly Ala Val Gly Lys
        915                 920                 925

Val Val Pro Phe Phe Glu Ala Lys Val Val Asp Leu Asp Thr Gly Lys
    930                 935                 940

Thr Leu Gly Val Asn Gln Arg Gly Glu Leu Cys Val Arg Gly Pro Met
945                 950                 955                 960

Ile Met Ser Gly Tyr Val Asn Asn Pro Glu Ala Thr Asn Ala Leu Ile
                965                 970                 975

Asp Lys Asp Gly Trp Leu His Ser Gly Asp Ile Ala Tyr Trp Asp Glu
            980                 985                 990

Asp Glu His Phe Phe Ile Val Asp Arg Leu Lys Ser Leu Ile Lys Tyr
        995                 1000                1005

Lys Gly Tyr Gln Val Ala Pro Ala Glu Leu Glu Ser Ile Leu Leu Gln
    1010                1015                1020

His Pro Asn Ile Phe Asp Ala Gly Val Ala Gly Leu Pro Asp Asp Asp
1025                1030                1035                1040

Ala Gly Glu Leu Pro Ala Ala Val Val Val Leu Glu His Gly Lys Thr
                1045                1050                1055

Met Thr Glu Lys Glu Ile Val Asp Tyr Val Ala Ser Gln Val Thr Thr
            1060                1065                1070

Ala Lys Lys Leu Arg Gly Gly Val Val Phe Val Asp Glu Val Pro Lys
        1075                1080                1085

Gly Leu Thr Gly Lys Leu Asp Ala Arg Lys Ile Arg Glu Ile Leu Ile
    1090                1095                1100

Lys Ala Lys Lys Gly Gly Lys Ile Ala Val
1105                1110

<210> SEQ ID NO 6
<211> LENGTH: 1114
<212> TYPE: PRT
<213> ORGANISM: Artificial Sequence
<220> FEATURE:
<223> OTHER INFORMATION: Description of Artificial Sequence: Synthetic
```

-continued

Construct

<400> SEQUENCE: 6

```
Met Asp Val Val Asn Gln Leu Val Ala Gly Gly Gln Phe Arg Val Val
1               5                   10                  15

Lys Glu Pro Leu Gly Phe Val Lys Val Leu Gln Trp Val Phe Ala Ile
            20                  25                  30

Phe Ala Phe Ala Thr Cys Gly Ser Tyr Thr Gly Glu Leu Arg Leu Ser
        35                  40                  45

Val Glu Cys Ala Asn Lys Thr Glu Ser Ala Leu Asn Ile Glu Val Glu
    50                  55                  60

Phe Glu Tyr Pro Phe Arg Leu His Gln Val Tyr Phe Asp Ala Pro Ser
65                  70                  75                  80

Cys Val Lys Gly Gly Thr Thr Lys Ile Phe Leu Val Gly Asp Tyr Ser
                85                  90                  95

Ser Ser Ala Glu Phe Phe Val Thr Val Ala Val Phe Ala Phe Leu Tyr
            100                 105                 110

Ser Met Gly Ala Leu Ala Thr Tyr Ile Phe Leu Gln Asn Lys Tyr Arg
        115                 120                 125

Glu Asn Asn Lys Gly Pro Met Met Asp Phe Leu Ala Thr Ala Val Phe
    130                 135                 140

Ala Phe Met Trp Leu Val Ser Ser Ala Trp Ala Lys Gly Leu Ser
145                 150                 155                 160

Asp Val Lys Met Ala Thr Asp Pro Glu Asn Ile Ile Lys Glu Met Pro
                165                 170                 175

Met Cys Arg Gln Thr Gly Asn Thr Cys Lys Glu Leu Arg Asp Pro Val
            180                 185                 190

Thr Ser Gly Leu Asn Thr Ser Val Val Phe Gly Phe Leu Asn Leu Val
        195                 200                 205

Leu Trp Val Gly Asn Leu Trp Phe Val Phe Lys Glu Thr Gly Trp Ala
    210                 215                 220

Ala Pro Phe Met Arg Ala Pro Pro Gly Ala Pro Glu Lys Gln Pro Ala
225                 230                 235                 240

Pro Gly Asp Ala Tyr Gly Asp Ala Gly Tyr Gly Gln Gly Pro Gly Gly
                245                 250                 255

Tyr Gly Pro Gln Asp Ser Tyr Gly Pro Gln Gly Gly Tyr Gln Pro Asp
            260                 265                 270

Tyr Gly Gln Pro Ala Ser Gly Gly Gly Tyr Gly Pro Gln Gly Asp
        275                 280                 285

Tyr Gly Gln Gln Gly Tyr Gly Gln Gln Gly Ala Pro Thr Ser Phe Ser
    290                 295                 300

Asn Gln Met Gly Ser Thr Ser Asn Gly Arg Gln Cys Ala Gly Ile Leu
305                 310                 315                 320

Gln Ile Ser Met Val Ser Lys Gly Glu Glu Asp Asn Met Ala Ile Ile
                325                 330                 335

Lys Glu Phe Met Arg Phe Lys Val His Met Glu Gly Ser Val Asn Gly
            340                 345                 350

His Glu Phe Glu Ile Glu Gly Glu Gly Glu Gly Arg Pro Tyr Glu Gly
        355                 360                 365

Thr Gln Thr Ala Lys Leu Lys Val Thr Lys Gly Gly Pro Leu Pro Phe
    370                 375                 380

Ala Trp Asp Ile Leu Ser Pro Gln Phe Met Tyr Gly Ser Lys Ala Tyr
385                 390                 395                 400
```

Val Lys His Pro Ala Asp Ile Pro Asp Tyr Leu Lys Leu Ser Phe Pro
                405                 410                 415
Glu Gly Phe Lys Trp Glu Arg Val Met Asn Phe Glu Asp Gly Gly Val
            420                 425                 430
Val Thr Val Thr Gln Asp Ser Ser Leu Gln Asp Gly Glu Phe Ile Tyr
        435                 440                 445
Lys Val Lys Leu Arg Gly Thr Asn Phe Pro Ser Asp Gly Pro Val Met
    450                 455                 460
Gln Lys Lys Thr Met Gly Trp Glu Ala Ser Ser Glu Arg Met Tyr Pro
465                 470                 475                 480
Glu Asp Gly Ala Leu Lys Gly Glu Ile Lys Gln Arg Leu Lys Leu Lys
                485                 490                 495
Asp Gly Gly His Tyr Asp Ala Glu Val Lys Thr Thr Tyr Lys Ala Lys
            500                 505                 510
Lys Pro Val Gln Leu Pro Gly Ala Tyr Asn Val Asn Ile Lys Leu Asp
        515                 520                 525
Ile Thr Ser His Asn Glu Asp Tyr Thr Ile Val Glu Gln Tyr Glu Arg
    530                 535                 540
Ala Glu Gly Arg His Ser Thr Gly Gly Met Asp Glu Leu Tyr Lys Gly
545                 550                 555                 560
Pro Val Leu Ala Met Glu Asp Ala Lys Asn Ile Lys Lys Gly Pro Ala
                565                 570                 575
Pro Phe Tyr Pro Leu Glu Asp Gly Thr Ala Gly Glu Gln Leu His Lys
            580                 585                 590
Ala Met Lys Arg Tyr Ala Leu Val Pro Gly Thr Ile Ala Phe Thr Asp
        595                 600                 605
Ala His Ile Glu Val Asn Ile Thr Tyr Ala Glu Tyr Phe Glu Met Ser
    610                 615                 620
Val Arg Leu Ala Glu Ala Met Lys Arg Tyr Gly Leu Asn Thr Asn His
625                 630                 635                 640
Arg Ile Val Val Cys Ser Glu Asn Ser Leu Gln Phe Phe Met Pro Val
                645                 650                 655
Leu Gly Ala Leu Phe Ile Gly Val Ala Val Ala Pro Ala Asn Asp Ile
            660                 665                 670
Tyr Asn Glu Arg Glu Leu Leu Asn Ser Met Asn Ile Ser Gln Pro Thr
        675                 680                 685
Val Val Phe Val Ser Lys Lys Gly Leu Gln Lys Ile Leu Asn Val Gln
    690                 695                 700
Lys Lys Leu Pro Ile Ile Gln Lys Ile Ile Met Asp Ser Lys Thr
705                 710                 715                 720
Asp Tyr Gln Gly Phe Gln Ser Met Tyr Thr Phe Val Thr Ser His Leu
                725                 730                 735
Pro Pro Gly Phe Asn Glu Tyr Asp Phe Val Pro Glu Ser Phe Asp Arg
            740                 745                 750
Asp Lys Thr Ile Ala Leu Ile Met Asn Ser Ser Gly Ser Thr Gly Leu
        755                 760                 765
Pro Lys Gly Val Ala Leu Pro His Arg Ala Leu Cys Val Arg Phe Ser
    770                 775                 780
His Ala Arg Asp Pro Ile Phe Gly Asn Gln Ile Ala Pro Asp Thr Ala
785                 790                 795                 800
Ile Leu Ser Val Val Pro Phe His His Gly Phe Gly Met Phe Thr Thr
                805                 810                 815
Leu Gly Tyr Leu Ile Cys Gly Phe Arg Val Val Leu Met Tyr Arg Phe 820                 825                 830
Glu Glu Glu Leu Phe Leu Arg Ser Leu Gln Asp Tyr Lys Ile Gln Ser
            835                 840                 845
Ala Leu Leu Val Pro Thr Leu Phe Ser Phe Leu Ala Lys Ser Thr Leu
        850                 855                 860
Ile Asp Lys Tyr Asp Leu Ser Asn Leu His Glu Ile Ala Ser Gly Gly
865                 870                 875                 880
Ala Pro Leu Ser Lys Glu Val Gly Glu Ala Val Ala Lys Arg Phe His
            885                 890                 895
Leu Pro Gly Ile Arg Gln Gly Tyr Gly Leu Thr Glu Thr Thr Ser Ala
        900                 905                 910
Ile Leu Ile Thr Pro Lys Gly Asp Asp Lys Pro Gly Ala Val Gly Lys
            915                 920                 925
Val Val Pro Phe Phe Glu Ala Lys Val Val Asp Leu Asp Thr Gly Lys
        930                 935                 940
Thr Leu Gly Val Asn Gln Arg Gly Glu Leu Cys Val Arg Gly Pro Met
945                 950                 955                 960
Ile Met Ser Gly Tyr Val Asn Asn Pro Glu Ala Thr Asn Ala Leu Ile
                965                 970                 975
Asp Lys Asp Gly Trp Leu His Ser Gly Asp Leu Ala Tyr Trp Asp Glu
            980                 985                 990
Asp Glu His Phe Phe Ile Val Gly Arg Leu Lys Ser Leu Ile Lys Tyr
            995                 1000                1005
Lys Gly Tyr Gln Val Ala Pro Ala Glu Leu Glu Ser Ile Leu Leu Gln
        1010                1015                1020
His Pro Asn Ile Phe Asp Ala Gly Val Ala Gly Leu Pro Asp Asp Asp
1025                1030                1035                1040
Ala Gly Glu Leu Pro Ala Ala Val Val Val Leu Glu His Gly Lys Thr
            1045                1050                1055
Met Thr Glu Lys Glu Ile Val Asp Tyr Val Ala Ser Gln Val Thr Thr
                1060                1065                1070
Ala Lys Lys Leu Arg Gly Gly Val Val Phe Val Asp Glu Val Pro Lys
            1075                1080                1085
Gly Leu Thr Gly Lys Leu Asp Ala Arg Lys Ile Arg Glu Ile Leu Ile
        1090                1095                1100
Lys Ala Lys Lys Gly Gly Lys Ile Ala Val
1105                1110

<210> SEQ ID NO 7
<211> LENGTH: 3345
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 7
atggacgtgg tgaatcagct ggtggctggg ggtcagttcc gggtggtcaa ggagcccctt      60
ggcttcgtga aggtgctgca gtgggtcttt gccatcttcg cctttgctac gtgtggcagc     120
tacaccgggg agcttcggct gagcgtggag tgtgccaaca agacggagag tgccctcaac     180
atcgaagttg aattcgagta ccccttcagg ctgcaccaag tgtactttga tgcaccctcc     240
tgcgtcaaag ggggcactac caagatcttc ctggttgggg actactcctc gtcggctgaa     300
ttctttgtca ccgtggctgt gtttgccttc ctctactcca tggggccct ggccacctac     360

```
atcttcctgc agaacaagta ccgagagaac aacaaagggc ctatgatgga ctttctggct    420
acagccgtgt tcgctttcat gtggctagtt agttcatcag cctgggccaa aggcctgtcc    480
gatgtgaaga tggccacgga cccagagaac attatcaagg agatgcccat gtgccgccag    540
acagggaaca catgcaagga actgagggac cctgtgactt caggactcaa cacctcagtg    600
gtgtttggct tcctgaacct ggtgctctgg gttggcaact tatggttcgt gttcaaggag    660
acaggctggg cagccccatt catgcgcgca cctccaggcg ccccggaaaa gcaaccagca    720
cctggcgatg cctacggcga tgcgggctac gggcagggcc ccggaggcta tgggccccaa    780
gactcctacg ggcctcaggg tggttatcaa cccgattacg ggcagccagc cagcggtggc    840
ggtggctacg ggcctcaggg cgactatggg cagcaaggct atggccaaca gggtgcgccc    900
acctccttct ccaatcagat gggatccact agtaacggcc gccagtgtgc tggaattctg    960
cagatatcga tggtgagcaa gggcgaggag ataacatgg ccatcatcaa ggagttcatg    1020
cgcttcaagg tgcacatgga gggctccgtg aacggccacg agttcgagat cgagggcgag    1080
ggcgagggcc gcccctacga gggcacccag accgccaagc tgaaggtgac caagggtggc    1140
cccctgccct tcgcctggga catcctgtcc cctcagttca tgtacggctc caaggcctac    1200
gtgaagcacc ccgccgacat ccccgactac ttgaagctgt ccttcccccga gggcttcaag    1260 tgggagcgcg tgatgaactt cgaggacggc ggcgtggtga ccgtgaccca ggactcctcc    1320
ctgcaggacg gcgagttcat ctacaaggtg aagctgcgcg gcaccaactt cccctccgac    1380
ggccccgtaa tgcagaagaa gaccatgggc tgggaggcct cctccgagcg gatgtacccc    1440
gaggacggcg ccctgaaggg cgagatcaag cagaggctga agctgaagga cggcggccac    1500
tacgacgctg aggtcaagac cacctacaag gccaagaagc ccgtgcagct gcccggcgcc    1560
tacaacgtca acatcaagtt ggacatcacc tcccacaacg aggactacac catcgtggaa    1620
cagtacgaac gcgccgaggg ccgccactcc accggcggca tggacgagct gtacaaggga    1680
ccggtgctag cgatggaaga cgccaaaaac ataaagaaag cccggcgcc attctatcct    1740 ctagaggatg gaaccgctgg agagcaactg cataaggcta tgaagagata cgccctggtt    1800
cctggaacaa ttgcttttac agatgcacat atcgaggtga acatcacgta cgcggaatac    1860
ttcgaaatgt ccgttcggtt ggcagaagct atgaaacgat atgggctgaa tacaaatcac    1920
agaatcgtcg tatgcagtga aaactctctt caattcttta tgccggtgtt gggcgcgtta    1980
tttatcggag ttgcagttgc gcccgcgaac gacatttata tgaacgtga attgctcaac    2040 agtatgaaca tttcgcagcc taccgtagtg tttgtttcca aaaggggggtt gcaaaaaatt    2100 ttgaacgtgc aaaaaaaatt accaataatc cagaaaatta ttatcatgga ttctaaaacg    2160
gattaccagg gatttcagtc gatgtacacg ttcgtcacat ctcatctacc tcccggtttt    2220
aatgaatacg attttgtacc agagtccttt gatcgtgaca aaacaattgc actgataatg    2280
aattcctctg gatctactgg gttacctaag ggtgtggccc ttccgcatag agctctctgc    2340
gtcagattct cgcacgccag agatccaata tttggcaatc aaatcgctcc ggatactgcg    2400
attttaagtg ttgttccatt ccatcacggt tttggaatgt ttactacact cggatatttg    2460
atatgtggat ttcgagtcgt cttaatgtat agatttgaag aagagctgtt tttacgatcc    2520
cttcaggatt acaaaattca agtgcgttg ctagtaccaa cccctatttt cattcttggcc    2580 aaaagtactc tgattgacaa atacgattta tctaatttac acgaaattgc ttctggggcc    2640
gcacctcttt cgaaagaagt cggggaagcg gttgcaaaac gcttccatct tccagggata    2700
cgacaaggat atgggctcac tgagactact agtgctattc tgattacacc caagggggat    2760
```

```
gataaaccgg gcgcggtcgg taaagttgtt ccattttttg aagcgaaggt tgtggatctg    2820
gataccggga aaacgctggg cgttaatcag agaggcgaat tatgtgtcag aggacctatg    2880
attatgtccg gttatgtaaa caatccggaa gcgaccaacg ccttgattga caaggatgga    2940
tggctacatt ctggagacct agcttactgg gacgaagacg aacacttctt catagttggc    3000
cgcttgaagt ctttaattaa atacaaagga tatcaggtgg cccccgctga attggaatcg    3060
atattgttac aacaccccaa catcttcgac gcgggcgtgg caggtcttcc cgacgatgac    3120
gccggtgaac ttcccgccgc cgttgttgtt ttggagcacg gaaagacgat gacggaaaaa    3180
gagatcgtgg attacgtcgc cagtcaagta acaaccgcga aaaagttgcg cggaggagtt    3240
gtgtttgtgg acgaagtacc gaaaggtctt accggaaaac tcgacgcaag aaaaatcaga    3300
gagatcctca taaaggccaa gaagggcgga aagatcgccg tgtaa                   3345
```

QUANTITATIVE GENETICALLY ENCODED OPTICAL REPORTER CONSTRUCT

CROSS-REFERENCE TO RELATED APPLICATION

This application is a continuation-in-part of International Application PCT/US10/52787, filed Oct. 15, 2012, which claims the benefit of U.S. Provisional Application Ser. No. 61/252,262, filed Oct. 16, 2009. This application claims the benefit of the filing dates of each of these applications and the entire disclosures of these applications are incorporated by reference as if set forth fully herein.

BACKGROUND

The regulation and maintenance of energy is an important topic of investigation in the biomedical sciences. One area of particular interest is the mechanism associated with energy regulation and maintenance at synaptic terminals.

Synaptic terminals are the key portals of information flow between brain cells, and they are subcellular regions with high energy demands. They are the sites of transduction of electrical information into chemical information (on the presynaptic side) followed by a reconversion of chemical information into electrical information (on the postsynaptic side). Both of these processes require the use of adenosine-tri-phosphate (ATP). ATP is also needed to support membrane trafficking events in the form of synaptic vesicle fusion, endocytosis and filling with neurotransmitters. As a consequence of these high metabolic needs, most synapses in the brain have one or two mitochondria anchored within the presynaptic terminals.

The precise regulation of ATP levels at synapses, and the general field of synaptic metabolism are poorly understood. This low level of understanding is unfortunate, because dysfunction of synaptic metabolism, which includes potential mitochondrial dysfunction may be linked to a number of neurological or neurodegenerative diseases such as Parkinson's and Alzheimer's disease. Thus, understanding and identifying the molecular mechanisms responsible for the fidelity of synaptic transmission in the central nervous system is a subject of intense interest.

One area that has remained very poorly explored is how local synaptic adenosine-tri-phosphate concentrations ([ATP]) are controlled. This area is particularly interesting because although in response to intense energy demands, many tissues in the body rely on local glycogen stores as a source of energy, neurons lack the capacity to store glycogen.

Synapses in particular have intense energy needs that vary enormously over time. During periods of intense activity such as with sustained action potential firing, the energy requirements at synapses increase significantly, because in addition to regulating ion homeostasis, the many membrane trafficking steps associated with both pre- and postsynaptic biology all have significant ATP requirements.

Moreover, because synapses are typically located at significant distances from neuronal cell bodies, they must rely on local energy resources to function. The presence of local mitochondria at many synapses suggests that there must be a local response to energy demands mediated through oxidative phosphorylation. However, it is important to note that, in hippocampal CA1 axons for example, only approximately 50% of synapses appear to have local mitochondria [1]. Thus, a number of important questions remain open regarding the nature of the relationship between activity and local [ATP]: is local depletion of [ATP] responsible for certain forms of activity-dependent synaptic depression?; how does the absence or presence of local mitochondria impact activity-dependent changes in [ATP]?; and do certain diseased states of the nervous system function manifest as a deregulation of local ATP supplies?

Upon review of these open questions, regulation of local [ATP] becomes a clear area of significant importance and interest. Furthermore, the need to understand this important biological variable is underscored by the large coterie of neurological disorders (e.g., peripheral neuropathies and ataxias) [2] that result from mutations in mitochondrial genes. Unfortunately, although measurements of ATP in living tissue are routinely made, in general these are made for large volumes. This is problematic because synaptic terminals are relatively small, having volumes of only about $10^{-15}$ [1], and current technologies have not been amenable to measurements in these subcellular specializations.

A direct measure of the molecular currency of energy supply in cells, the concentration of ATP, would provide the most useful diagnostic for examining energy homeostasis in living tissues. If one could provide a quantitative analytical tool to begin to directly monitor intracellular synaptic [ATP] levels, new avenues of research in synaptic energetics, a poorly explored but critically important problem in understanding brain function would be opened. The present invention is directed to providing new and non-obvious compositions and methods to probe the dynamics of ATP levels at synapses.

SUMMARY OF THE INVENTION

The present invention provides compositions and methods for measuring the local concentration of ATP in e.g., cells. Through the novel and non-obvious compositions and methods, one can better study ATP use and regulation at different locales, including but not limited to at or near synapses.

In one embodiment, the present invention provides an isolated polynucleotide comprising a sequence that encodes a hybrid protein, wherein the sequence comprises a first region that encodes a reporter enzyme, a second region that encodes a reporter fluorescent protein and third region that encodes a targeting protein, wherein these genes are linked together in a single reading frame. The targeting protein is capable of causing the protein that contains regions that correspond to each of the regions of the construct to be in a desired locale of e.g., a cell. The isolated polynucleotide may be single stranded or double stranded and DNA, RNA or a DNA/RNA hybrid. Furthermore, the polynucleotide may be isolated (and purified), which unless otherwise specified includes but is not limited to as part of a vector such as a plasmid or bacteriophage.

In another embodiment, the present invention is directed to a hybrid protein that is encoded by a polynucleotide. The hybrid protein may be encoded by the polynucleotide of the present invention or otherwise created (e.g., through chemical synthesis) to have the same sequence as a protein created through enzymatic synthesis that relies on one of the polynucleotides of the present invention. The protein may have each of a first region, second region and third region that corresponds to the three aforementioned regions of the polynucleotide construct.

In another embodiment, the present invention provides an isolated polynucleotide comprising a sequence that encodes a hybrid protein, wherein the sequence comprises a first region that encodes a reporter enzyme that is capable of reporter activity such as in a cell or within a locale of a cell by for example, chemoluminescence, and a second region that encodes a reporter fluorescent protein. These two regions may be linked in a single reading frame. In some embodiments, the present invention is directed to proteins with amino acid sequences that are the same as this hybrid protein. By way of example, there may be a hybrid protein that comprises, consists essentially of or consists of the amino acid sequence of a reporter enzyme and the amino acid sequence of a fluorescent reporter protein. In some embodiments, the construct also contains a nucleotide sequence of a targeting protein; however, in other embodiments it does not. These hybrid proteins may provide a direct measure of enzyme activity to enzyme concentration. These proteins may be particularly advantageous for an enzyme whose activity can be related to luminescence, e.g., in ATP assays.

In another embodiment, the present invention provides a reporter construct and methods for its use for the in vivo or in vitro measurement of the concentration of a specific biologically important molecule in a subcellular compartment or locale. This reporter construct comprises three genes linked together in a single reading frame to produce a hybrid protein when expressed in a suitable biological system. The reporter construct is a genetically-encoded hybrid nucleic acid molecule comprising, consisting essentially of or consisting of three parts:

(1) a gene encoding an enzyme that senses the molecule to be measured;
(2) a gene encoding a fluorescent protein; and
(3) a gene encoding a targeting protein to enrich the concentration of the reporter in the desired subcellular location of interest.

The gene that encodes an enzyme that senses the molecule to be measured will typically interact with the analyte of interest. Preferably, it will form an easily measurable result. The gene that encodes a fluorescent protein will provide a measure of the amount of the reporter enzyme at the site of interest. Thus the components (1) and (2) provide a way to calibrate the enzymatic measurements. The ratio of the enzyme activity to the fluorescence provides a measure of the specific activity of the enzyme. Component (3) enables the detection of such local concentrations by targeting these reporter molecules to the subcellular location of interest.

A particular embodiment of this invention is a construct that can be used to measure the ATP concentration ([ATP]) in living presynaptic nerve terminals. The components of this construct may comprise, consist essentially of or consist of: (1) a gene encoding the enzyme luciferase from the North American firefly *Photonis pyralis* (SEQ ID NO: 1); (2) a gene encoding any of a variety of fluorescent proteins, e.g., mCherry (SEQ ID NO: 2); and (3) a gene encoding the synaptic vesicle transmembrane protein synaptophysin (SEQ ID NO: 3) in a single reading frame. This construct is referred to as Syn-ATP for synaptically-targeted fluorescent-protein-tagged luciferase and in some embodiments, may contain linking nucleotides between three genes.

The protein that Syn-ATP expresses is depicted in use in FIG. 1 in the context of a synaptic vesicle. The incorporation of synaptophysin results in a much higher local concentration of luciferase in nerve terminals than would exist were the protein not present. This feature allows for the measurements of luciferase activity locally at nerve terminals. Feature (2) provides a means by which to determine the local concentration of synaptically-targeted luciferase. This allows one to normalize the measured luciferase output, thereby allowing a local measurement of ATP concentration at the nerve terminals.

The selected genes also offer the following benefits. The luciferase enzyme has three substrates, ATP, $Mg^{2+}$ and the membrane-permeant molecule luciferin, and the enzyme catalyzes the production of oxyluciferin, which emits a photon in the visible spectrum as shown in FIG. 2. Hence, in the presence of saturating luciferin, the photon emission provides a direct measure of the ATP concentration.

The fluorescent protein provides a measure of the enzyme concentration. Preferably, this protein should have good optical properties, such as a low photobleaching rate constant and insensitivity to changes in pH and calcium ion concentration, which are two variables that are known to fluctuate during biological activity. mCherry is known to have these desirable properties. However, the aforementioned gene is merely an example and the gene for other fluorescent proteins can be used. Examples of other genes include, but are not limited to, Green Fluorescent Protein (GFP) from *Aequorea victoria*, GFP mutants, and various GFP-like green, yellow and red proteins.

Synaptophysin is one of approximately nine different types of transmembrane proteins that are highly enriched on synaptic vesicles. It is a tetra-spanning membrane protein whose N and C termini are both located on the cytoplasmic face of the protein.

The nucleic acid construct for this hybrid gene is then transfected into primary neurons. After a suitable time to allow for expression, the fluorescence (e.g., mCherry) can be visualized using fluorescence microscopy where the expression will follow that of native synaptophysin and become localized to nerve terminals. Upon addition of cell-permeant luciferin, the substrate for the luciferase enzyme, one can then image the chemoluminescence that arises from individual nerve terminals. The detected photon flux arising from each nerve terminal can be normalized with respect to the fluorescence obtained from the fluorescent protein. This effectively corrects for differences in the number of luciferase molecules at each location. Chemoluminescence is imaged using the same apparatus as the fluorescence, however no excitation source is used during the detection of light.

In other embodiments, the present invention provides constructs in which one or more nucleotides have been substituted in order to generate proteins that have one or more amino acids that are substituted as compared to amino acids in one or more of the first region, the second region or the third region of other embodiments of the present invention. In still other embodiments, the present invention provides mutant (also referred to as modified) hybrid proteins in which one or more of amino acids have been substituted as compared to one or more of the protein regions of the aforementioned hybrid protein. These modifications may for example, be incorporated into the first region and render the protein usable and suitable for both live cell measurements and in situ calibration at 37° C. These probes may for example, be used to monitor the dynamics of ATP concentration during neuronal action potential firing.

In some embodiments, the polynucleotide and resulting protein can be used in isolated neurons to measure the ATP concentration at synaptic vesicles under various conditions for research purposes. For example, they can help to determine if synaptic [ATP] under resting or active conditions is derived from glycolysis or oxidative phosphorylation or whether local mitochondria can account for synaptic activity. By observing [ATP] changes between two different experimental states, this method can also be employed to screen for molecules that perturb or enhance synaptic metabolism, as well as to investigate the synaptic metabolism in diseased and normal states of brain function.

In some embodiments the polynucleotide and resulting protein can be used to measure ATP concentrations in any type of cell either in a specific sub-cellular location or throughout the entire intracellular volume. Here, again, by observing [ATP] changes in such cells between two different experimental states, this method can also be employed to screen for molecules that perturb or enhance the [ATP]s being studied.

Additionally, the constructs and proteins of the present invention can be used in assays in which drugs that enhance ATP production, including but not limited to AICAR, AICA Riboside and GW 501516 or combinations thereof are administered prior to and/or during the time in which measurements are taken.

In another embodiment, the present invention is directed to a method for measuring ATP concentrations in general. The method comprises: (1) transfecting a cell with polynucleotides of the present invention or otherwise associating a hybrid protein of the present invention with a cell (e.g. a neuron) at a desired locale; (2) exposing the cell to luciferin; (3) measuring fluorescence; (4) measuring chemoluminescence; and (5) calculating [ATP]. The exposing may for example, be done under saturation conditions and the calculation of the concentration may for example, be done by determining the ratio of luminescence to fluorescence and comparing this ratio to a suitably constructed calibration curve.

In another embodiment, the present invention provides a method for determining the in vivo concentration of a molecule in a subcellular compartment or locale. The method comprises transfecting one or more cells with a subcellular locale of interest with a nucleic acid of the present invention; allowing time for the expression of a protein encoded by the construct in the one or more cells; measuring fluorescence of the fluorescent protein and measuring activity of a reporter enzyme in the one or more cells of interest; and determining a ratio of enzyme activity to fluorescence.

In some embodiments, the protein of the present invention can be used to monitor the dynamics of ATP concentration during neuronal action potential firing. Additionally or in alternative embodiments, the protein of the present invention (and the polynucleotide that encodes it) can be used to show that resting presynpatic ATP levels depend on continuous glycolysis but that during action potential firing, ATP generated by oxidative phosphorylation in mitochondria is important.

BRIEF DESCRIPTION OF THE DRAWINGS

FIG. 4 shows a bioluminescence image obtained after expression of non-targeted luciferase. The left panel is a fluorescence image of the distribution of a fluorescently-tagged synaptic vesicle protein in a single neuron. The box shows a fluorescent punctum representing an individual nerve terminal. The neuron was expressing free luciferase. The right hand image is the resulting bioluminescent image resulting from the luciferase activity when the cell was incubated with 10 mM luciferin and photons acquired over a ten min period. Useable signal is only apparent in the cell body and the proximal dendrites; no signal above background can be observed in the nerve terminals.

DETAILED DESCRIPTION OF THE INVENTION

Figure 1:
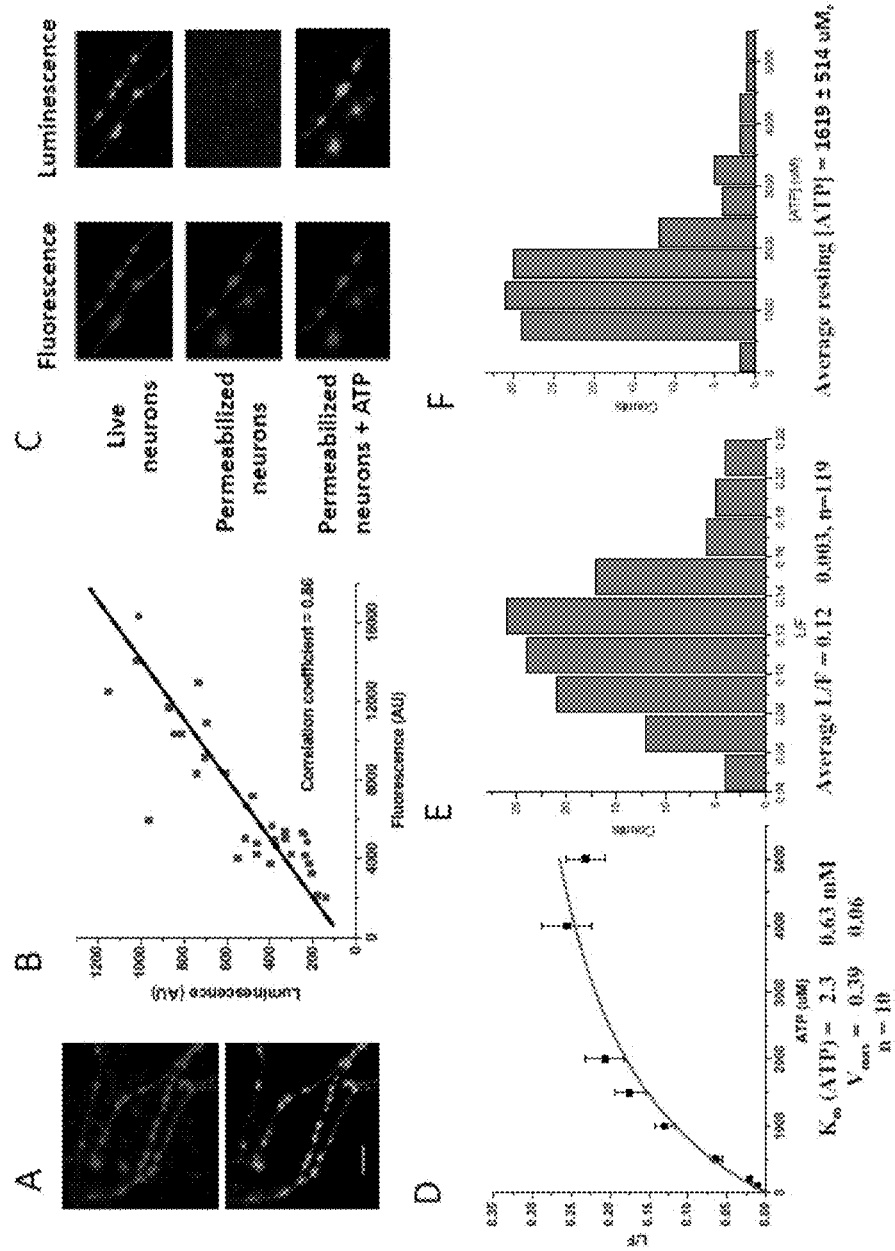
FIG. 1 is a representation of Syn-ATP, which is a hybrid reporter molecule that encodes an ATP sensor, luciferase (Luc), a fluorescent protein mCherry (mCh) and a synaptic vesicle protein, synaptophysin (Syn). Expression of this reporter protein results in targeting of this fluorescent-luminescent reporter to nerve terminals.

In the following description, reference is made to the accompanying drawings and figures that form a part hereof. The drawings and figures show by way of illustration, specific embodiments that may be practiced. These embodiments are described in detail in order to enable those skilled in the art to practice the invention, and it is to be understood that other embodiments may be utilized and that structural and logical changes may be made without departing from the scope of the present invention. The following description of example embodiments is, therefore, not to be taken in a limited sense, and the scope of the present invention is defined by the appended claims, which are intended to encompass the full scope of equivalents to which they may be entitled.

In some embodiments, the present invention is directed to reporter constructs that are useful for the in vivo or in vitro measurement of the concentration of specific biologically important molecules in a subcellular compartment or locale. These constructs may comprise, consist essentially of or consist of nucleotide sequences. In other embodiments, the present invention is directed to the protein that is encoded by these constructs or that has the same sequence as a protein encoded by these constructs. In still other embodiments, the present invention is directed to methods for use of these constructs and proteins.

The reporter construct may comprise three genes linked together in a single reading frame to produce a hybrid protein when expressed in a suitable biological system. Thus, the reporter construct may be a genetically-encoded hybrid nucleic acid molecule consisting of three regions. The first region may encode a gene for an enzyme that senses the molecule to be measured. This enzyme may interact with the analyte of interest and form an easily measurable result. The second region may encode a gene for a fluorescent protein. This protein may provide a measure of the amount of reporter enzyme at the site of interest. The third region may encode a gene for a targeting protein to enrich the concentration of the reporter in the desired subcellular location of interest.

The first two regions code for protein sequences that provide a way to calibrate the enzymatic measurements. The ratio of the enzyme activity to the fluorescence essentially provides the specific activity of the enzyme. The third region encodes a protein that enables the detection of local concentrations by targeting these reporter molecules to the subcellular location of interest.

A specific embodiment of this invention is a construct that can be used to measure the adenosine-tri-phosphate (ATP) concentration ([ATP]) in vivo in subcellular locations that offers significant improvements over current approaches for measuring [ATP].

Current Approaches for Measuring [ATP]

Traditional estimates of intracellular [ATP] concentration have generally been indirect, relying on either absorbance measurements of HPLC separated lysates of cellular material or bioluminescence of luciferase derived from large population of cells. It is from these measurements that other researches have indirectly accounted for the total content of luciferase (Gajewski, C. D., Yang, L., Schon, E. A., and Manfredi, G. (2003) Mol Biol Cell 14, 3628-3635).

More recently two different optical approaches have been introduced based on the use of fluorescent proteins. Unfortunately, both have serious drawbacks with respect to providing a quantitative readout of ATP levels. The first, pericam, takes advantage a circularly permuted GFP to splice in a bacterial ATP-binding protein (GlnK1) as the ATP sensor (Berg, J., Hung, Y. P., and Yellen, G. (2009) Nat Methods 6, 161-166). The proximity of the binding protein to the GFP chromophore rendered the optical properties of the GFP molecule sensitive to the ATP binding in the sensor. Although an elegant approach, it suffers primarily from the fact that GlnK1 binds ATP very tightly, with reported Kd for ATP binding <100 nM, far below the range of intracellular [ATP] typically reported (0.1-1 mM). Thus, this type of sensor would be expected to be saturated under most physiological conditions. The authors of that work, however, noted that in the presence of ADP there is a significant competitive inhibition for ATP binding, and the reporter can provide a reasonable measure of the ATP/ADP ratio. Although this might prove useful for some circumstances, it is generally thought that ADP is rapidly hydrolyzed to AMP in the cellular milieu, and thus the reporter will probably remain saturated with ATP.

The second approach (Imamura, H., Huynh Nhat, K. P., Togawa, H., Saito, K., Iino, R., Kato-Yamada, Y., Nagai, T., and Noji, H. (2009) *Proc Natl Acad Sci USA*) made use of a different ATP sensor, the $\epsilon\square$-subunit of the F0-F1 ATPase, and combined it with a FRET pair (CFP-YFP) to create a sensor termed ATeam. This sensor suffers from three difficulties that will hinder its use for quantitative applications. Although the authors were able to generate four different variants of the $\epsilon$-subunit harboring different point mutations, none of the respective Km's were in the appropriate range for the expected approximately 0.1-1 mM range of intracellular ATP. This problem is compounded by the fact that the reporter shows a non-linear readout with respect to [ATP], with a hill coefficient of approximately 2. As a result, the dynamic range is quite limited because the system reaches saturation quickly in the vicinity of the Km.

Thus, at present no suitable methods exist to probe the dynamics of [ATP] at subcellular resolution, and in particular at the level of single synapses. The need to understand this important biological variable is underscored by the large coterie of neurological disorders (e.g., peripheral neuropathies, ataxias and neurodegenerative diseases) (Chen, H., and Chan, D. C. (2006) Curr Opin Cell Biol 18, 453-459 and Petrozzi, L., Ricci, G., Giglioli, N. J., Siciliano, G., and Mancuso, M. (2007) Biosci Rep 27, 87-104) that result from mutations in mitochondrial genes. Providing a quantitative analytical tool to begin to directly monitor intracellular synaptic [ATP] levels should open up new avenues of research in synaptic energy metabolism, a poorly explored but critically important problem in understanding brain function.

Constructs, Proteins and Methods of Use

In some embodiments, the present invention provides a nucleic acid reporter construct that enables the measurement of [ATP] at presynaptic nerve terminals and methods of its use. This reporter construct has the following components linked together in a single reading frame: (1) a gene encoding the enzyme luciferase from the North American firefly *Photonis pyralis*; (2) a gene encoding any of the variety of fluorescent proteins; and (3) a gene encoding the synaptic vesicle transmembrane protein synaptophysin. As noted above, this construct and various modifications with a similar use are referred to as Syn-ATP. The protein that it expresses is depicted in use in FIG. 1 in the context of a synaptic vesicle. This protein is a synaptically-targeted fluorescent-protein-tagged luciferase.

Various embodiments of the proteins of the present invention possess one or more if not all of the following properties: (1) a good signal to noise ratio when sampling local synaptic ATP levels (at the single synapse level) over a useful time scale; (2) sensitivity to [ATP] in a useful biological range; (3) relative insensitivity to other environmental variables such as calcium ions and pH or other nucleotides; (4) allowing for calibration to determine absolute ATP levels and provide meaningful comparisons of [ATP] from synapse to synapse and from cell to cell; (5) the ability to provide a report of ATP levels that does not significantly alter native physiological properties of the synapse; and (6) being genetically encoded.

Figure 2:
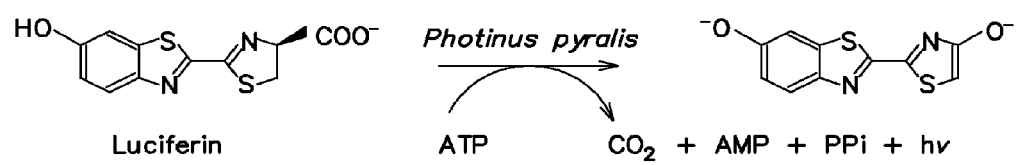
FIG. 2 is representation of luciferase chemistry.

The use of the Syn-ATP nucleic acid reporter construct takes advantage of recent significant technological improvements in optical detection, in particular at the level of image sensors, to be able to image chemiluminescence at the subcellular level. This approach utilizes the 62 kD enzyme luciferase from the firefly *Photinus pyralis* that converts luciferin, a cell permeant substrate, to oxyluciferin+light in the form of visible spectrum photon in an ATP-dependent fashion (FIG. 2).

Luciferases have previously been shown to be very useful and robust ATP sensors in cells (Bell, C. J., Manfredi, G., Griffiths, E. J., and Rutter, G. A. (2007) *Methods Cell Biol* 80, 341-352) and faithfully follow Michaelis-Menten kinetics with respect to ATP concentration. However, their use for examining subcellular ATP levels, and in particular synaptic ATP concentrations, poses a technological challenge, given the typical very slow catalytic rate (only photon at a rate of approximately one per second) for most ATP-dependent luciferases. Although chemiluminescence has been mapped at the subcellular level in applications such as bioluminescence energy transfer (BRET) (Coulon, V., Audet, M., Homburger, V., Bockaert, J., Fagni, L., Bouvier, M., and Perroy, J. (2008) *Biophys J* 94, 1001-1009), the bioluminescent enzyme used in those cases is a luciferase from *Renilla reniformis*. This luciferase has a much higher turnover rate than that of *Photinus pyralis*, but sadly it does not use ATP or luciferin as a substrate, using coelenterazine and calcium ions instead.

Furthermore, as the local photon flux in a given subcellular area will be determined by the number of luciferase enzymes present, diffusion of the enzyme will begin to blur the spatial information on the microscopic scale even over timescales of approximately one second. The present invention overcomes these challenges by combining the molecular engineering of the Syn-ATP nucleic acid reporter construct with state-of-the-art optical detection.

In some embodiments, in order to overcome the difficulty of using a bioluminescence approach for sub-cellular quantitative imaging of ATP, the inventor has made two modifications to luciferase. The reporter construct was designed to express luciferase in neurons as a "double" chimeric protein, so that each luciferase was linked to a fluorescent protein and a protein that targets the luciferase to presynaptic terminals. The fluorescent protein component provides a ratiometric way to normalize luminescence signals with respect to fluorescent signals. The local ratio of luminescence to fluorescence thereby provides a means by which to correct the local photon flux in a given experiment and in a given part of the cell, thereby providing the local concentration of the enzyme.

The targeting component helps concentrate the enzyme in the region of interest. This improves the signals, because it increases the concentration of the reporter at the synapse. It also overcomes the problem of reporter diffusion, because by anchoring itself to synaptic vesicles it essentially immobilizes (or at least greatly slows diffusion) of the reporter. In some embodiments, mCherry is advantageous as the fluorescent tag, because it is conveniently spectrally well separated from the typical GFP channel such that a number of useful functional synaptic reporters (e.g., pHluorin or genetically encoded calcium indicators) can be used in tandem. Although in principle mCherry could serve as an energy acceptor for luciferase emission via BRET, this should not impose any problem, as all emitted photons will be detected in the chemiluminescence mode without spectral separation. The targeting protein selected is synaptophysin, a tetra-spanning synaptic vesicle membrane protein of poorly understood function. Because this component anchors the reporter protein to synaptic vesicles it also overcomes the problem of reporter diffusion, because it essentially immobilizes (or at least greatly slows diffusion) of the reporter protein.

Expression of Syn-ATP in neurons results in excellent synaptic localization, as synaptophysin is quite specifically located in presynaptic nerve terminals. Results of a typical experiment are illustrated in FIG. 4. A typical experiment consists of expression of the construct in neurons followed by image acquisition in both luminescence and fluorescence channels. The fluorescence image provides a map of the concentration of Syn-ATP throughout the axon. Prior to gathering the bioluminescence image, a saturating concentration of luciferin is applied to the preparation. One advantage of luminescence as compared to fluorescence is that because it does not involve any illumination with excitation light, the non-specific background arises purely from stray light impinging upon the image sensor, as well as any dark noise or readout noise associated with the acquisition. This differs from the noise associated with imaging very dim fluorescence signals. In that case in addition to the aforementioned sources of noise, one ultimately faces the problem of cellular autofluorescence. With luminescence this is eliminated; the only source of chemiluminescence will be the expressed luciferase molecules. Suitable optimization of the detection strategy with elimination of all possible sources of stray light and a judicious choice of detectors to eliminate camera noise allows high signal to noise ratio information to be obtained.

The ratio of the luminescence intensities to the fluorescence intensities provides a "map" of the luciferase specific activity across different boutons. If luciferin itself is maintained at saturating levels, the specific activity is proportional to the concentration of ATP providing one is near or below the $K_m$ of luciferase for ATP.

As persons of ordinary skill in the art will recognize, luciferases are slow enzymes, and therefore photon fluxes obtained will be far lower than with conventional fluorescence approaches. However as the inventor appreciated, sufficient photon fluxes can be generated with Syn-ATP to provide the desired subcellular [ATP] measurements.

The nucleic acid construct for this hybrid gene is then transfected into primary neurons. After a suitable time to allow for expression, the mCherry fluorescence can be visualized using fluorescence microscopy where the expression will follow that of native synaptophysin and become localized to nerve terminals. Upon addition of cell-permeant luciferin, the substrate for the luciferase enzyme, one can then image the chemoluminescence arising from individual nerve terminals. The detected photon flux arising from each nerve terminal can be normalized with respect to the fluorescence obtained from the fluorescent protein. This effectively corrects for differences in the number of luciferase molecules at each location. Chemiluminescence is imaged using the same apparatus as the fluorescence, however no excitation source is used during the detection of light.

This construct can be used in isolated neurons to measure the ATP concentration at synaptic vesicles under various conditions for research purposes. This method can also be employed to screen for compounds that perturb or enhance synaptic metabolism by performing the [ATP] measurements both in the presence and absence of test compounds to determine whether the [ATP] differs when the compound is present. This method can also be used to investigate the synaptic metabolism in diseased and normal states of brain function.

It will be appreciated by those skilled in the art that the components of Syn-ATP can be modified in various ways, and the Syn-ATP construct will have the same utility. For example, the gene for the luciferase enzyme can be altered to make it more thermo-stable, including but not limited to, by containing any or all of the mutations shown to improve the thermostability including Thr214Ala, Ala215Leu, Ile232Ala, Phe295Leu, and Glu354Lys (Branchini B R et al. Anal. Biochem. 361, 253 (2007)). As persons of ordinary skill in the art are aware, by introducing specific mutations to a polynucleotide sequence, a desired mutation can be introduced to the protein that is produced from that mutation. Polynucleotide constructs or proteins that differ from Syn-ATP by one or more of these mutations may be referred to as "mutant Syn-ATP," and unless otherwise specified or apparent from context, the ability to use Syn-ATP in an application implies the ability to use mutant Syn-ATP as well.

Similarly the gene (and protein) can be modified in ways to enhance luciferase's enzymatic activity. One such example of this would be to encode the luciferase with the Ile423Leu mutation that has been shown to increase the turnover rate of this enzyme (Fuji H. et al. Anal. Biochem. 366, 131 (2007). Similarly any mutant identified in a mutagenesis screen on bacterially-expressed "optimized" *Photinus pyrallis* luciferase with increases in the enzymes $k_{cat}$ and/or $K_m$ could be employed for the luciferase component of the Syn-ATP construct.

In other embodiments of the Syn-ATP construct, any gene encoding any fluorescent protein that has spectral properties compatible with the fluorescence and luminescence measurements can be used in this Syn-ATP construct. Other fluorescent proteins include but are not limited to Green Fluorescent protein, GFP, mPlum, mCherry, tdTomato, mStrawberry, J-Red, DsRed-monomer, mOrange, mKO, mCitrine, Venus, YPet, EYFP, Emerald, EGFP, CyPet, mCFPm, Cerulean, and T-Sapphire and combinations thereof.

Other embodiments of the Syn-ATP construct could contain the gene for any protein that is expressed specifically in the synaptic vesicles instead of synaptophysin. Other possible proteins that could be encoded in the Syn-ATP construct to target this reporter construct to the synaptic vesicles include but are not limited to: SV2, synapsin I, synapsin II, synaptotagmin (p65), vesicle associated membrane protein (synaptobrevin, VAMP), rab3A, VAT-1, vacuolar protein pump, and high MW proteoglycan.

Figure 3:
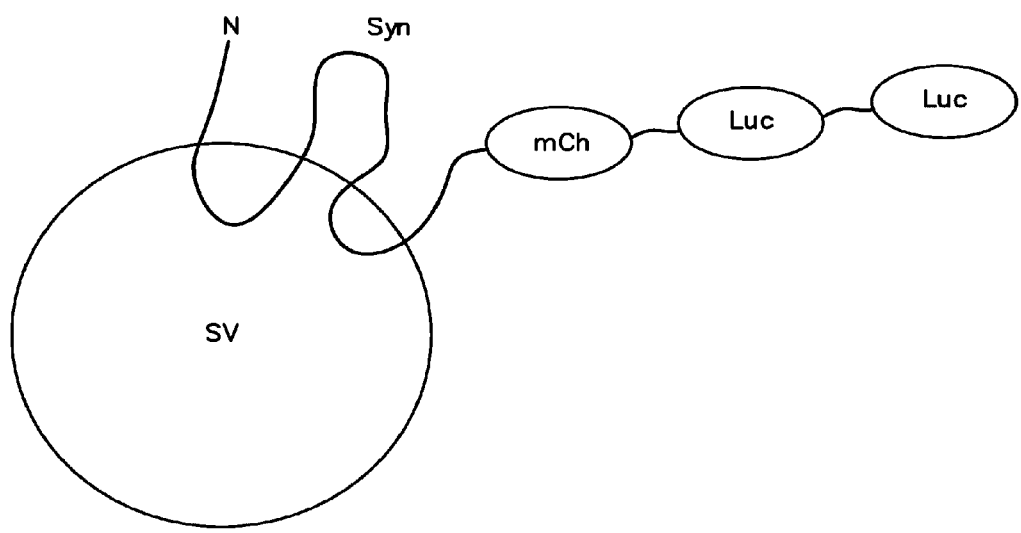
FIG. 3 is a representation of a Syn-ATP reporter protein with concatenated luciferases. The Syn-ATP construct has concatenated luciferase genes that would lead to expression of protein with increased total photon flux.

Another modification would be to increase the number of genes included in the construct for each different component. For example, a way to increase the concentration of expressed luciferase by the Syn-ATP reporter would be to include several genes for luciferase in tandem, i.e., concatemers (e.g., exactly or at least two, three, four, five or six) of luciferases in the construct. This would increase the total photon flux per expressed protein complex. Hence, another embodiment of the Syn-ATP construct of this invention includes a nucleic acid linking a gene encoding synaptophysin, a gene encoding a fluorescent protein such as mCherry to a string of more than one luciferase genes. A similar approach has been used successfully with fluorescent proteins, encoding a concatamer of up to 4 GFPs spliced into a protein (Zhu, Y., Xu, J., and Heinemann, S. F. (2009) Neuron 61, 397-411). The time resolution of the ATP mapping a Syn-ATP construct with three concatamers of luciferase will increase 3-fold (while maintaining the same signal to noise ratio). FIG. 3 depicts the synaptic vesicle-targeted protein with two concatenated luciferases.

Another embodiment of this invention is directed to the targeting of the luciferase-fluorescent protein construct so that one can measure the [ATP] at any other intracellular locale. Other intracellular locales of interest include post-synaptic spines that could be targeted by fusing the gene for the post synaptic density protein 95 (PSD-95) to the genes for the fluorescent protein and luciferase. PSD-95 is a scaffolding protein of the post synaptic density. Other non-neuronal intracellular locales where the study of local [ATP] would have physiological relevance include: the mitochondrial matrix, the cytoplasmic surface of mitochondria, the inner leaflet of the plasma membrane, the surface of the endoplasmic reticulum or the Golgi apparatus.

Employing the reporter construct of this invention helps to overcome the main barrier to using an enzyme as an optical reporter. In most optical readouts using fluorescence, the number of photons emitted per unit time sets the signal to noise ratio. Fluorescent reporters, such as small organic molecules or fluorescent proteins have a maximal light flux that is limited by the excited state lifetime of the molecule after it absorbs excitation light. For most fluorescent probes this is on the order of ten nsec. Thus, the maximal photon flux for typical probes, under maximal illumination intensity, is on the order of $10^8$ photons per sec. Enzymes work on much slower time scales and for a bioluminescent enzyme such as luciferase the maximal number of photons emitted is determined by the $k_{cat}$, that for *Photonus pyralis* luciferase is approximately 1.6 per sec. As a result in practice it is very difficult to use luciferase for subcellular imaging, because the maximal light output is $10^8$-fold lower than typical fluorescent probes.

Technological advances in recent years in imaging detectors have made the possibility of imaging extremely low photon fluxes a reality. However, given the very low turn-over rate for luciferase, it was not clear whether sufficient photons could be gathered in a useful time frame, and whether they would be greater in number than stray photons impinging on the detector over these time periods. In anticipation of this difficulty the data described here were all acquired using a state-of-the-art cooled electron multiplying charge coupled device camera (EMCCDs) with very high quantum efficiency and extremely low readout out noise, coupled to a high numerical aperture objective (40× fluar 1.3 NA) to maximize the total photon collection efficiency. Luminescence images were acquired in the absence of any dichroic or emission filters, and fluorescence images were obtained using a filter set optimized for mCherry detection that was alternately swung into the collection path.

FIG. 4 shows an example of the bioluminescent signal that can be obtained in a neuron expressing non-targeted luciferase. The neuron was co-transfected with a separate synaptic vesicle marker to allow one to visualize the nerve terminals. The luminescence image was obtained after incubating the neuron in saturating concentrations of luciferin and allowing the camera to integrate all emitted photons over a ten min period. Although weak luminescence signals could be obtained in the larger volume encompassed by the cell body, no detectable signal could be observed at the nerve terminals. Thus, even use of EMCCD detection and very long integration times does not allow detection of subcellular free luciferase bioluminescence.

Figure 5:
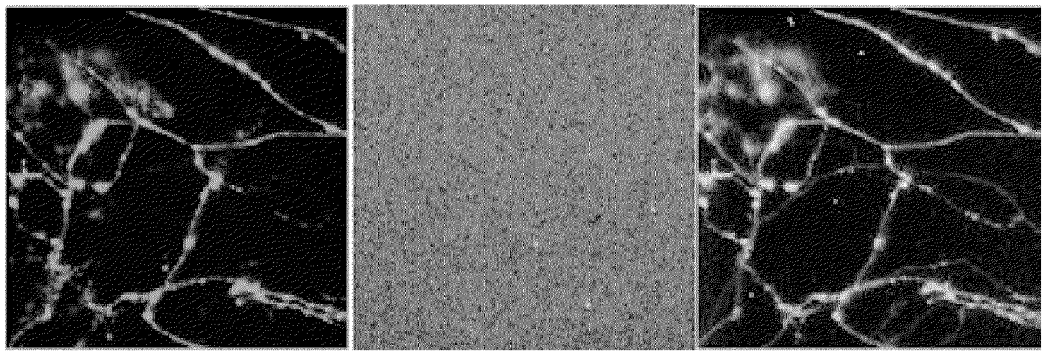
FIG. 5 is a representation of bioluminescence images. The figure shows that Syn-ATP gives robust bioluminescence images. The panel on the left shows the mCherry fluorescence channel of a neuron expressing Syn-ATP. The middle panel shows the bioluminescence image obtained in the absence of luciferin with a three minute integration time. The right panel shows a three minute bioluminescent image after incubation in 10 mM luciferin.

Using Syn-ATP, however, a much different picture emerges. FIG. 5 shows the type of image that can be obtained using Syn-ATP. In this case a neuron was transfected with Syn-ATP. The left panel shows the mCherry image showing a typical synaptic bouton-like distribution. The middle panel is the bioluminescent image that arises with a 3 min integration in the absence of luciferin. The right hand panel shows the same bioluminescence image with a three minute integration after incubation in saturating concentration of luciferin (10 mM).

These images demonstrate that targeting of luciferase to nerve terminals makes imaging of subcellular bioluminescence possible. The signal to noise ratio of the luminescence picture for the three minute integration time is approximately 40:1, which is calculated by comparing the mean value of the synaptic luminescence intensity compared to the standard deviation of the background noise in the absence of luciferin.

Figure 6:
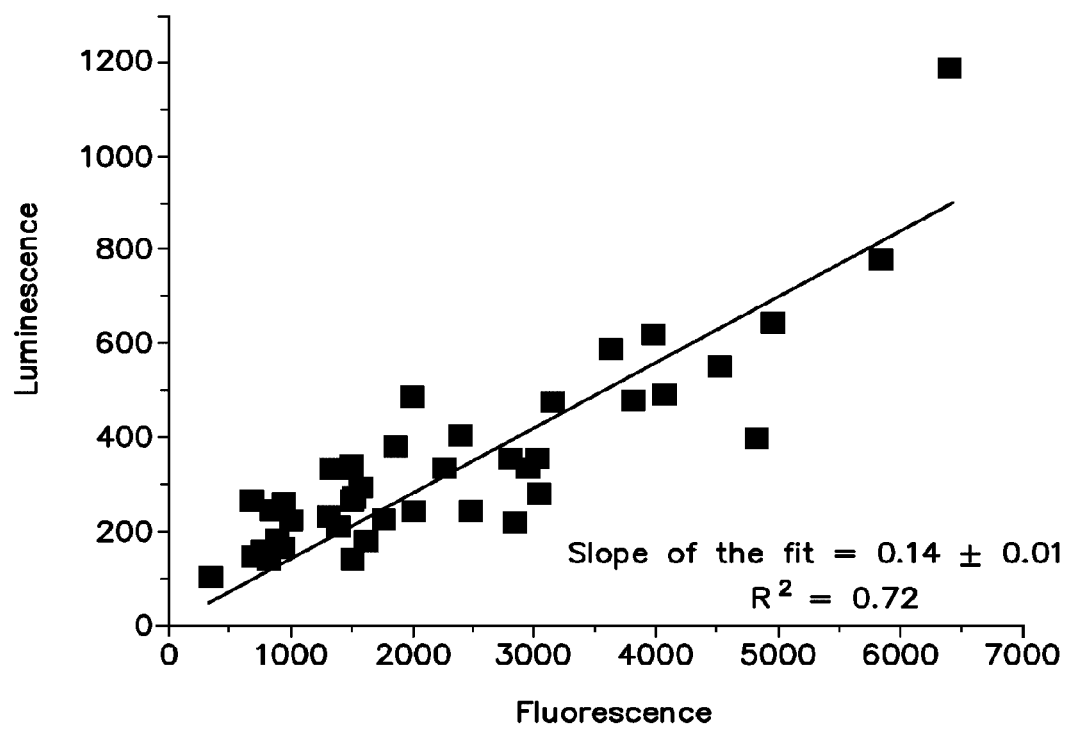
FIG. 6 shows Syn-ATP luminescence as correlated to fluorescence. The figure shows that luminescence is linearly proportional to the fluorescence intensity. The average intensity of the luminescence at different boutons is plotted as a function of the fluorescence intensity at the same boutons.

Analysis of the intensity of the luminescence signal as a function of the fluorescence signal across different boutons shows that the two signals are tightly correlated (FIG. 6). Thus, the ratio of the bioluminescence signal to the fluorescence signal should be proportional to the concentration of ATP under conditions where luciferin is saturating. The proportionality may not be strictly linear, as it will depend on where on the enzyme-substrate binding curve the physiological levels of [ATP] lie.

Methods for synthesizing the polynucleotides and proteins referred to herein include but are not limited to enzymatic synthesis and chemical synthesis.

EXAMPLES

The present description is further illustrated by the following examples, which should not be construed as limiting in any way. The contents of all cited references (including literature references, issued patents, and published patent applications as cited throughout this application) are hereby expressly incorporated by reference.

Example 1

Construction of Syn-ATP

The Syn-ATP shown in SEQ ID NO:4 was constructed using standard molecular biological tools and polymerase chain reaction (PCR) approaches to synthesize cDNA of the three fused genes that were then cloned into an expression vector. (See Sambrook J, Molecular Cloning: A Laboratory Manual, Third Edition, Cold Spring Harbor Press, 2001). It will be recognized by someone skilled in the art that various other sequences will have similar properties, and mutations in the sequences such as those already described are possible as long as the basic functions of each component remain. Similarly, different linking sequences between the component genes are possible, provided that the reading frames of the three component genes are maintained.

Example 2

Experimental Conditions for Transfection Experiments

All experiments were performed using dissociated primary hippocampal neurons according to procedures that have been previously described in Ryan T A. J. Neurosci 19:1317-1323 (1999). Briefly, hippocampi from newborn rats (P2-P4) were removed and dissected. Prior to cell dissociation, the dendate gyrus was removed leaving a relatively pure population of CA3 & CA1 excitatory neurons and interneurons. These cells were dissociated and plated onto poly-L-ornithine-coated glass cover slips and maintained in a $CO_2$/air incubator in growth media. cDNAs were transfected into the neurons using calcium-phosphate-mediated transfection as previously described (Sankaranarayanan S & Ryan T. A. Nature Cell Biol. 2, 197-204 (2000)) that has been optimized for simultaneously expressing multiple constructs in the same neuron. Transfection was carried out at day 7-10 in vitro (7-10 DIV), and experiments were performed between day 14 and 25 in vitro. For fluorescence and luminescence experiments cover slips were mounted in a rapid switching low volume perfusion chamber equipped with stimulus electrodes and mounted on the stage of an inverted microscope equipped with EMCCD detection and laser-based wide-field illumination. Chemiluminescence was imaged using the same apparatus as the fluorescence, however no excitation source was used during the detection of light.

Example 3

Luminescence and Fluorescence Detection

On DIV 14-25, neurons were mounted in a custom-built physiological perfusion chamber with temperature control that allows direct control of field stimulation to drive action potential firing. The perfusion chamber was mounted on a custom-built inverted microscope coupled to an EM-CCD camera with acousto-optically-gated wide-field laser illumination. Luminescence and fluorescence imaging were performed using an EM-CCD Andor Ixon, thinned back-illuminated sensor through a 1.3 NA 40× fluar objective. Neurons expressing Syn-ATP were perfused with 20 mM luciferin, one minute prior to and throughout the period during which the luminescence images was obtained. Luciferin is under saturating conditions for luciferase at this concentration. For optimal photon detection no optical elements other than a mirror and a tube lens (1.6×) are present in the light path during luminescence imaging. To minimize stray light contributions, the entire microscope is enclosed in a custom-built light-tight, shielded environment. Fluorescence images were obtained using acousto-optically-gated wide-field laser illumination, before and after the luminescence acquisition.

As mentioned earlier the sensitivity of luminescence imaging differs from conventional fluorescence imaging. In conventional imaging one is often limited in collecting sufficient photons from a sub-cellular region that are greater in number than those arising from auto-fluorescence in the tissue. In luminescence no excitation light is used. Consequently, the only photons originating from the tissue can be those associated with the bioluminescent reaction. However, given the low turnover rates of these enzymes, one will likely have to integrate over much longer times than for a typical fluorescence image. Here the biggest sources of noise will be stray light entering the microscope, dark noise associated with the detector and read-out noise associated with conversion of the charge into a voltage. Thus, a critical aspect in considering ultra-low photon flux imaging is to ensure that: (1) no stray-light enters the microscope; and (2) that the sensitivity of the camera is maximal (and therefore that instrumentation noise is kept to a minimum).

Although in general most fluorescence microscopes seek to eliminate possible stray light contamination, imaging of luminescence has far more stringent requirements as integration times will likely be over the tens or even hundreds of seconds time scale compared with approximately 100 msec or less with typical fluorescence measurements. Thus, photon contamination would need to be at least 2-3 orders of magnitude lower for luminescence measurements compared to fluorescence measurements. In order to maximize detection efficiency and minimize camera readout noise the inventor chose to use an electron-multiplying CCD as the imaging sensor. The high on-chip gain associated with the electron multiplication effectively lowers readout noise to negligible levels, and the current generation state-of-the-art EMCCDs have quantum efficiencies for photon detection in the visible spectrum of approximately 98%. Additionally, the dark noise is very low, allowing for use of long integration times.

Example 4

In Situ Calibration of Syn-ATP

Calibration for Estimates of $[ATP]_{syn}$

Figure 7:
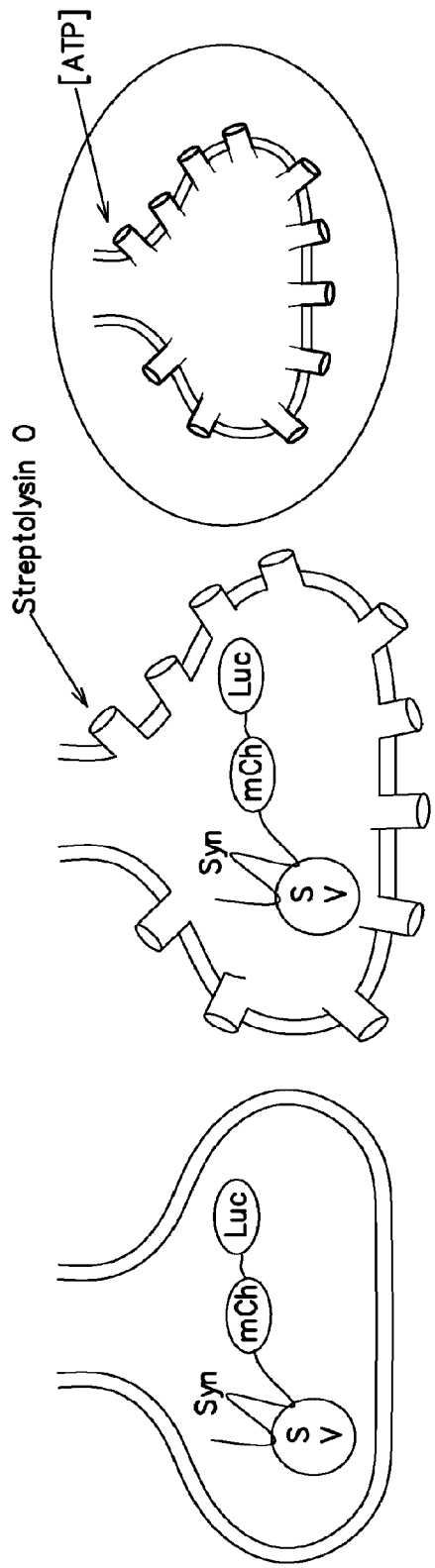
FIG. 7 is a representation of the in-situ calibration of Syn-ATP harboring the 5 mutations improving thermostability as well as the two catalytic mutations. (This version of Syn-ATP is referred to as TS__$_{t}$432L_D_436G or as Syn-ATP* herein). The figure shows permeabilization agents, such as streptolysin O, that selectively permeabilize the plasma membrane, and therefore should not significantly disrupt the distribution of Syn-ATP*, being used. After plasma membrane permeabilization ATP superfusion may be used to clamp the ATP concentration at different values. A series of these measurements from the same synapse may provide a full calibration curve.

In order to convert the ratio of luminescence per unit time to fluorescence (L/F) in Syn-ATP measurements into a value of [ATP] an in-situ calibration approach may be used. Application of mild cell permeabilization conditions allows the perfusion of extracellular ATP into the cytosol across the plasma membrane, thereby clamping the ATP-level to that of the bath (schematized in FIG. 7).

One advantage of the dual fluorescence-luminescence approach is that by monitoring the fluorescence at each synapse, one can effectively control for any loss of enzyme (because it is fluorescently-tagged) that might result from the permeabilization procedure. The key step here is to find conditions that leave the synaptic distribution of the enzyme itself reasonably intact. A number of permeabilized cell protocols have been developed over the years to allow the introduction of extracellular agents across the plasma membrane. This experiment used streptolysin-O, that forms approximately 20-30 nm pores in the plasma membrane. This small size of this toxin was thought to be sufficient to allow exchange of small molecules such as ATP. The presence of the pores in the plasma membrane allows extracellular [ATP] and intracellular [ATP] to equilibrate and be clamped to the external value. Using these permeabilization pores a standard curve was created for the luminescence/fluorescence ratio as a function of external [ATP] at each nerve terminal.

Figure 8:
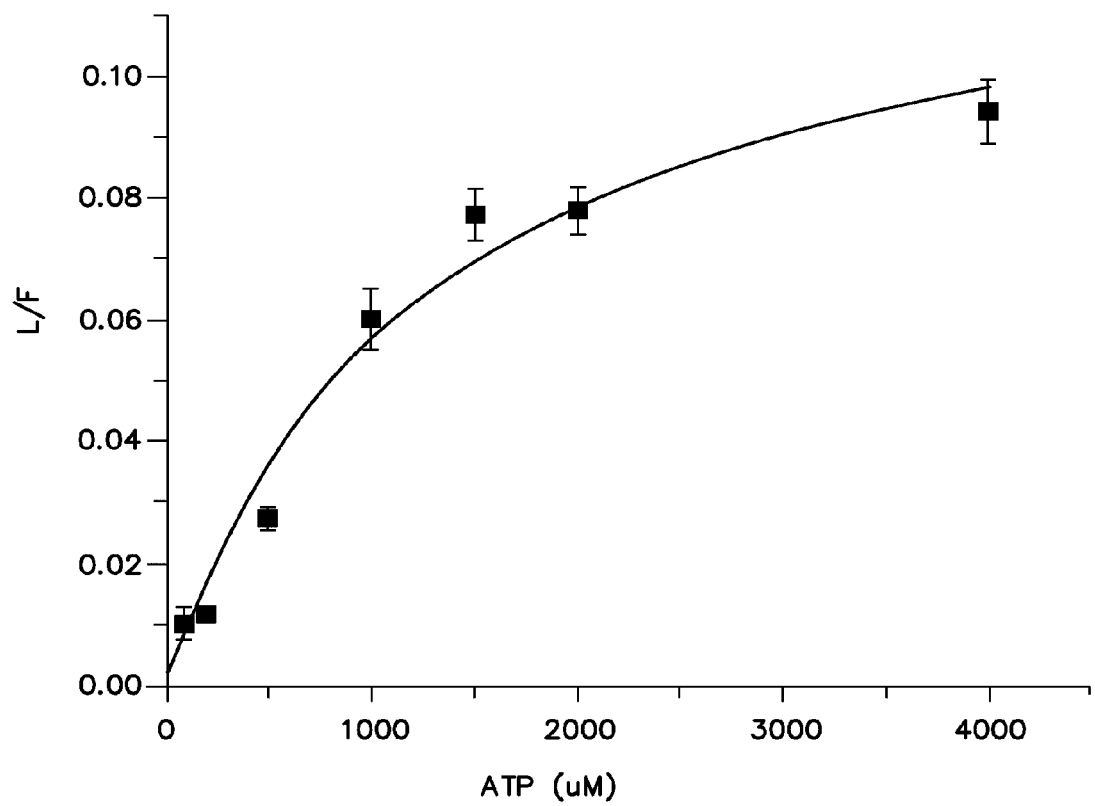
FIG. 8 is a mutant Syn-ATP* in-situ specific activity curve.

FIG. 8 shows a specific activity curve obtained from nerve terminals expressing Syn-ATP* with all of the Syn-ATP mutations described in Example 5 below (SEQ ID NO: 7-nucleotide sequence; SEQ ID NO: 6-amino acid sequence), permeabilized with streptolycin-O in the presence of 20 mM luciferin and varying ATP concentrations. The data were fit to a simple Michaelis-Menten relationship that indicates a Km ~2.1 mM for the reporter with respect to ATP concentration.

Notably, the increased stability of Syn-ATP under permeabilized cell conditions permits an accurate specific activity curve to be measured. This curve then permits the conversion of data obtained in live cells into absolute, calibrated values of ATP concentration.

Example 5

Mutations in Luciferase

Mutations in luciferase were used to optimize the construct: TS_I432L_D436G. The following set of mutations were incorporated, (i) five point mutations to increase thermal stability based on ref (1,2); T214A, A215L, I232A, F295L, E354K (these are referred to as TS mutations); (ii) increase in the catalytic rate of the enzyme by mutation I423L; and (iii) increase in the catalytic rate of the enzyme by mutation D436G.

Figure 9:
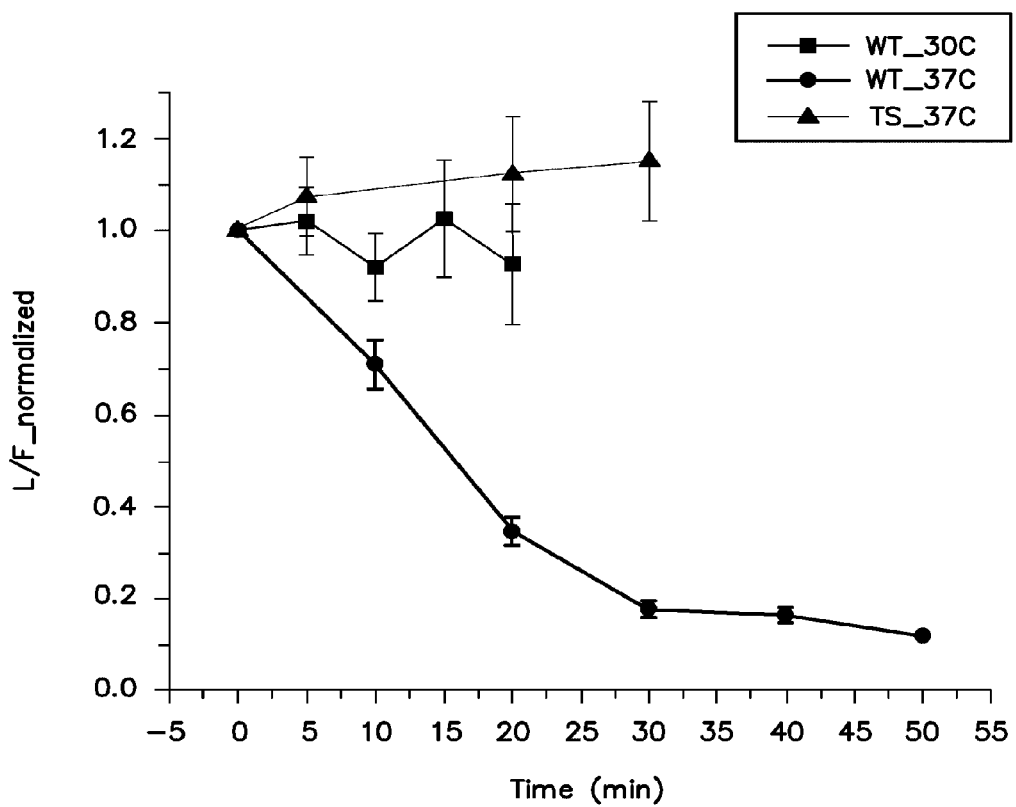
FIG. 9 is a graph that measures L/F normalized and plotted against time for a wild type protein at 30° C., a wild type protein at 37° C., and a thermostable mutant of the protein at 37° C. The figure demonstrates the effect of in situ calibration.

FIG. 9 shows in-situ calibration: at 37° C. the protein becomes very unstable after cell permeabilization (bottom curves in figures) and compared to 30° C., middle curve. These measurements were done after streptolycin-O-permeabilization (see FIG. 7). The rapid decay of enzymatic activity (plotted in FIG. 9 as the ratio of luminescence, L, to fluorescence, F, under these conditions for the wild type protein) precludes the ability to carry out a specific activity calibration curve. After introduction of the thermostability (TS) mutations, the activity is now stable under these conditions.

Figure 10:
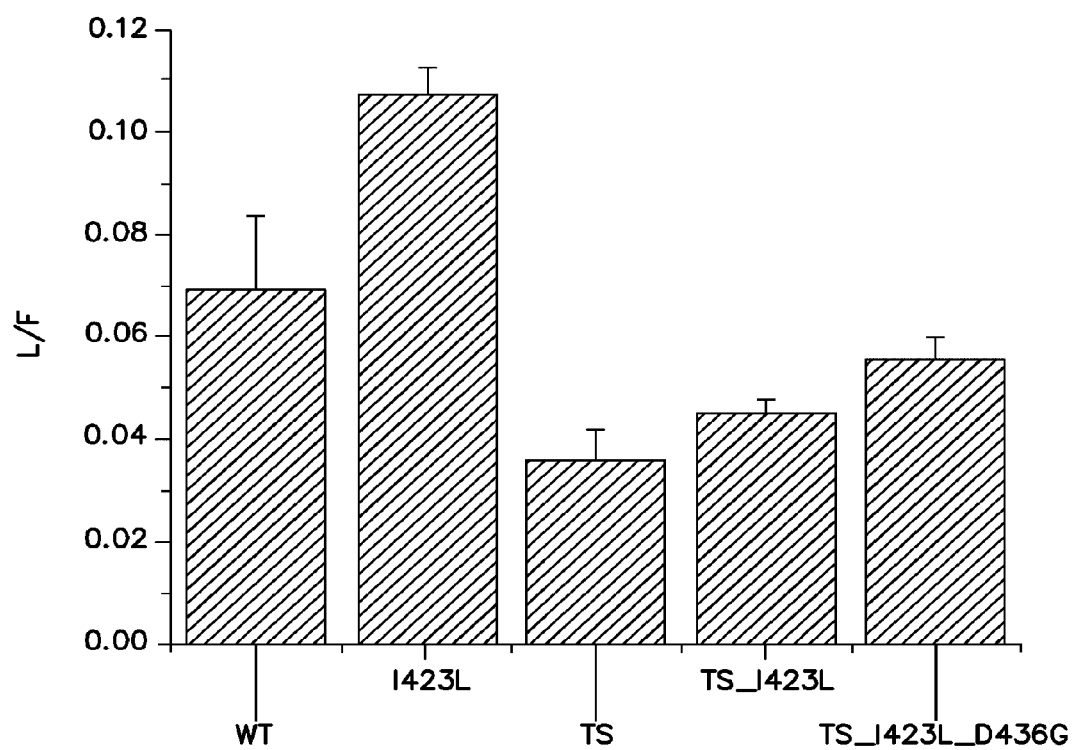
FIG. 10 is a representation of a bar graph that compares the enzymatic activity reported at resting intracellular synaptic ATP concentrations for the wild type and four mutants of Syn-ATP proteins.

A comparison was made of the enzymatic activity reported at resting intracellular synaptic ATP concentrations in intact synapses using various mutants of Syn-ATP at 37° C. The introduction of the TS mutants alone significantly lower the activity. However, introduction of the mutants that impact the enzyme's $k_{cat}$ restore the activity to near that of the WT protein, while permitting in-situ calibration that the wild type protein does not. The new mutant has the sequence of SEQ ID NO: 7. This mutant may be referred to as TS I432L_D 436G or Syn-ATP*. Results are shown in FIG. 10.

Example 6

Syn-ATP Activity Dependence of Luciferin

Figure 11:
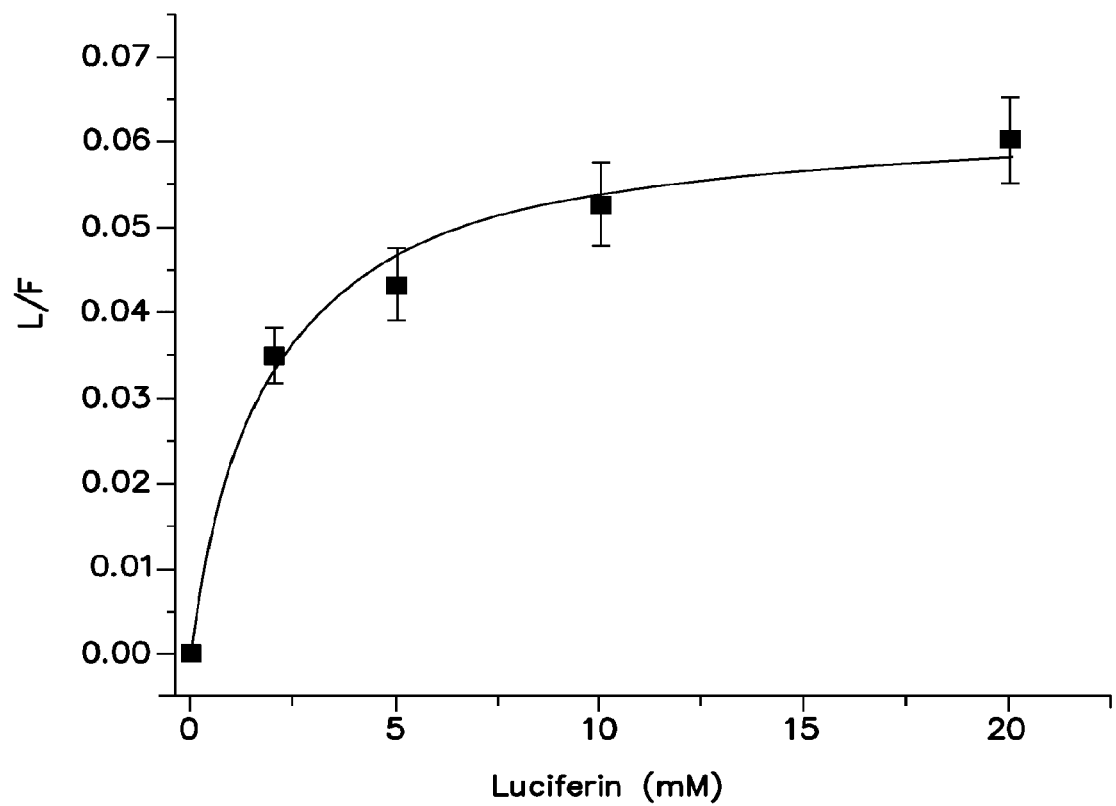
FIG. 11 is a curve that measures the L/F ratio, which is a measure of activity for a mutant Syn-ATP* against the concentration of luciferin (mM).

Experiments that were identical to those that were run to generate the data of FIG. 8 were performed keeping ATP fixed at 1 mM and varying the luciferin concentration. The data, as shown in FIG. 11, demonstrate that the signal from Syn-ATP* mutant is maximized at 20 mM luciferin. Those data form the basis for the specific activity curve shown, which was obtained from nerve terminals that expressed Syn-ATP mutant (SEQ ID NO: 6). The nerve terminals were permeabilized with streptolycin 0 in the presence of 1 mM ATP and varying luciferin concentrations. The data were fit to a simple Michaelis-Menton relationship indicating a Km of ~2 mM luciferin.

Example 7

Calcium Ion Concentration and pH

Syn-ATP* mutant activity (encoded by SEQ ID NO: 7, protein of SEQ ID NO: 6) in streptolycin-O permeabilized nerve terminals was examined for different calcium ion concentration and pH. These data show that calcium does not impact Syn-ATP signals but pH does. The calibration will allow appropriate corrections to be applied for intact cell experiments. For example, one may measure intracellular pH and determine possible changes in pH brought about by different physiological conditions, such as electrical stimulation, or the addition of pharmacological inhibitors. One can then correct any changes in the Syn-ATP* mutant readout for potential changes in pH according to the curve of FIG. 13.

Figure 12:
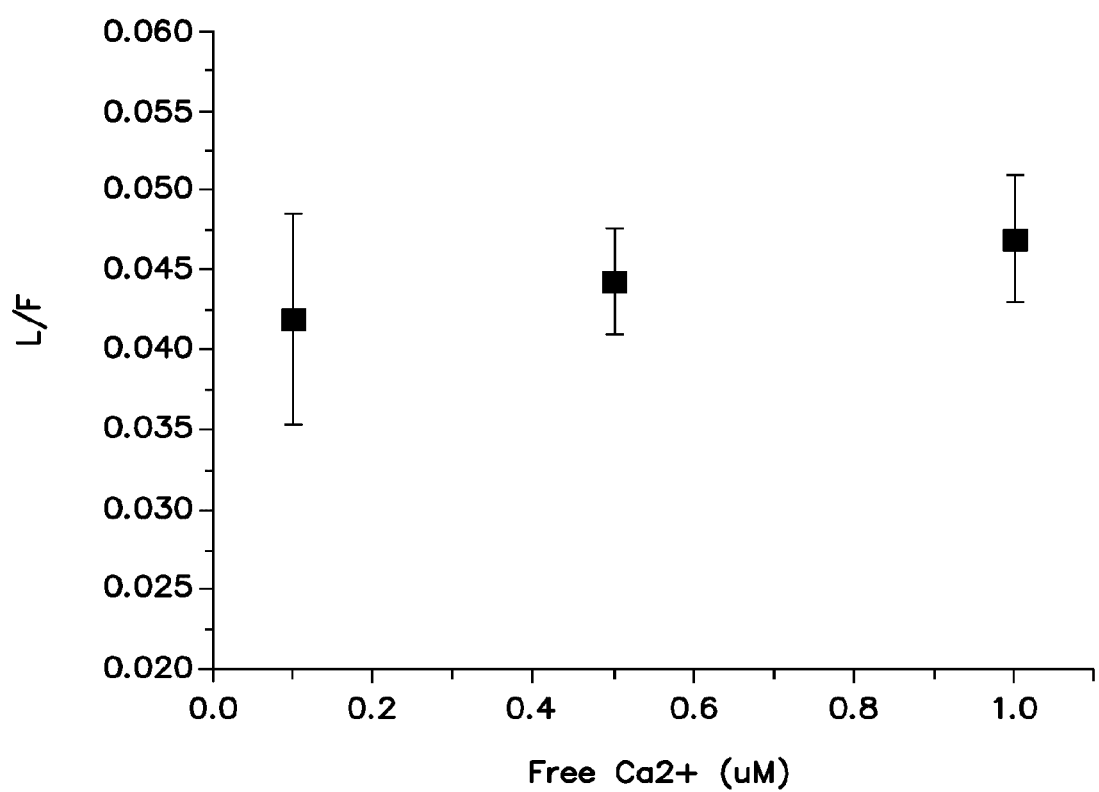
FIG. 12 is a representation of the measurement of a mutant Syn-ATP* activity (L/F ratio) in streptolycin-O permealized nerve terminals against free calcium ions.

As FIG. 12 shows, Syn-ATP* mutant activity at 20 mM luciferin and 1 mM ATP in streptolycin-O permeabilized nerve terminals with varying concentrations of calcium ions was measured. The data show that over the physiological range of calcium (0.1-1 µM) the signal is unchanged.

Figure 13:
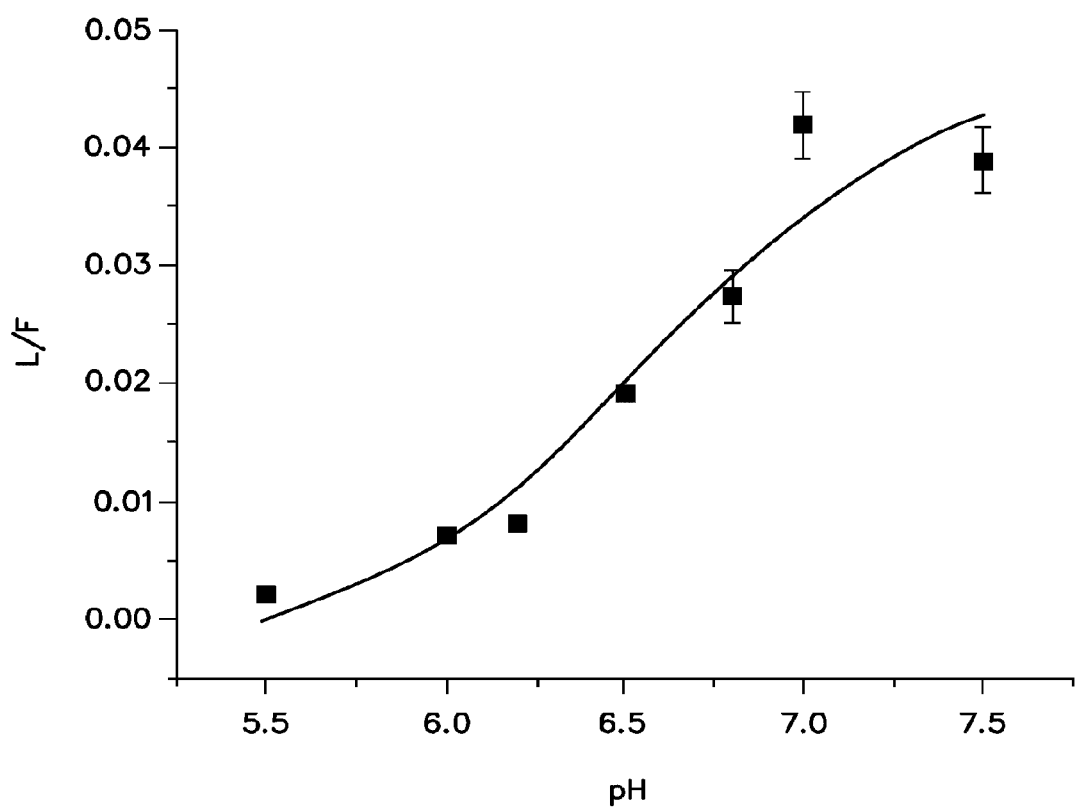
FIG. 13 is a representation of Syn-ATP* activity at 20 nM luciferin and 1 mM ATP in streptolycin-O permeabilized nerve terminals with varying pH.

As FIG. 13 shows, the Syn-ATP* activity at 20 mM luciferin and 1 mM ATP in streptolycin-O permeabilized nerve terminals with varying pH were measured. The data show that the reporter has a pH sensitivity with an apparent pK of approximately 6.6.

Example 8

Live Cell Syn-ATP Measurements

Live cell Syn-ATP measurements were taken. The measurements reveal that ATP concentrations depress during electrical activity. Primary hippocampal neurons were transfected with Syn-ATP* and mounted in custom-built a perfusion chamber (see previous examples). Syn-ATP measurements, luminescence and fluorescence images) were obtained at one minute intervals. After acquisition of the second time point, a sequence of action potentials were triggered by passing a brief electrical stimulus across a pair of field electrodes mounted on either side of the perfusion system for the time indicated in the figure (as described in reference [4]). Data from approximately 20 to approximately 30 synaptic terminals all originating from the same transfected neuron were obtained. For each synaptic terminal, the ratio of luminescence to fluorescence was calculated and the values for all terminals in the field of view were averaged together. All subsequent values obtained at different times were divided by the initial value at the first time point which was set to the value 1.

Example 9

Design Optimization and Calibration of Syn-ATP

Figures 14A, 14B, 14C, 14D, 14E, 14F:
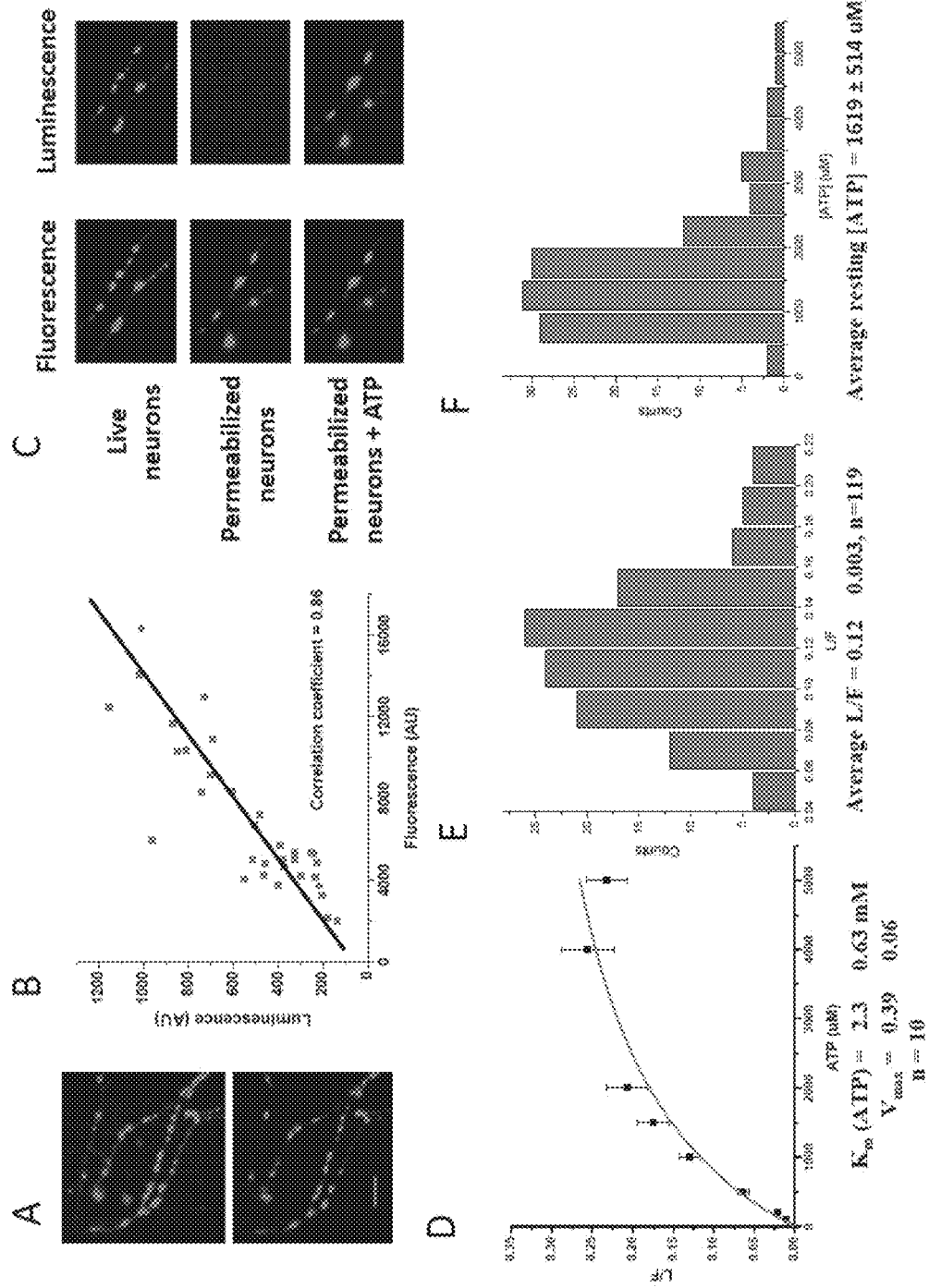
FIG. 14 is a representation of the application of Syn-ATP.

FIGS. 14A-14F show the basic application of Syn-ATP. FIG. 14A shows representative images of the fluorescence (dark gray—upper box) and luminescence (light gray—lower box) of an axonal branch of a neuron expressing this genetically encoded reporter. Neurons were bathed in luciferin, the substrate that produces light in the presence of applicant's reporter and ATP. The "spots" are individual synaptic terminals. FIG. 14B shows that the luminescence intensity is highly correlated with the fluorescence intensity. The slope of this correlation is related to the ATP concentration. FIG. 14C shows a procedure for calibrating the reporter to obtain the concentration of ATP in the nerve terminals. The procedure consists of 3 steps: (top) obtain a luminescence, fluorescence image pair in a live cell; (middle) permeabilize the neuron using streptolycin; This creates holes in the plasma membrane but does not disrupt the reporter, which is anchored to synaptic vesicles; (bottom) Add back ATP at a defined concentration and measure luminescence. Images are taken for a series of ATP concentrations. FIG. 14D takes the data obtained as in FIG. 14C, and as shown, from it, one can construct a calibration curve. These data are fit to a simple single binding site enzymatic relationship that relates the measured luminescence to fluorescence ratio (L/F) to ATP concentration. FIG. 14E shows measurements of the L/F values measured from a large distribution of cells. FIG. 14F shows the distribution of the equivalent ATP concentration based on the calibration in FIG. 14D, which indicates that the resting ATP values for nerve terminals is on average ~1.6 mM.

Example 10

Regulation of [ATP] at Rest

Figure 15:
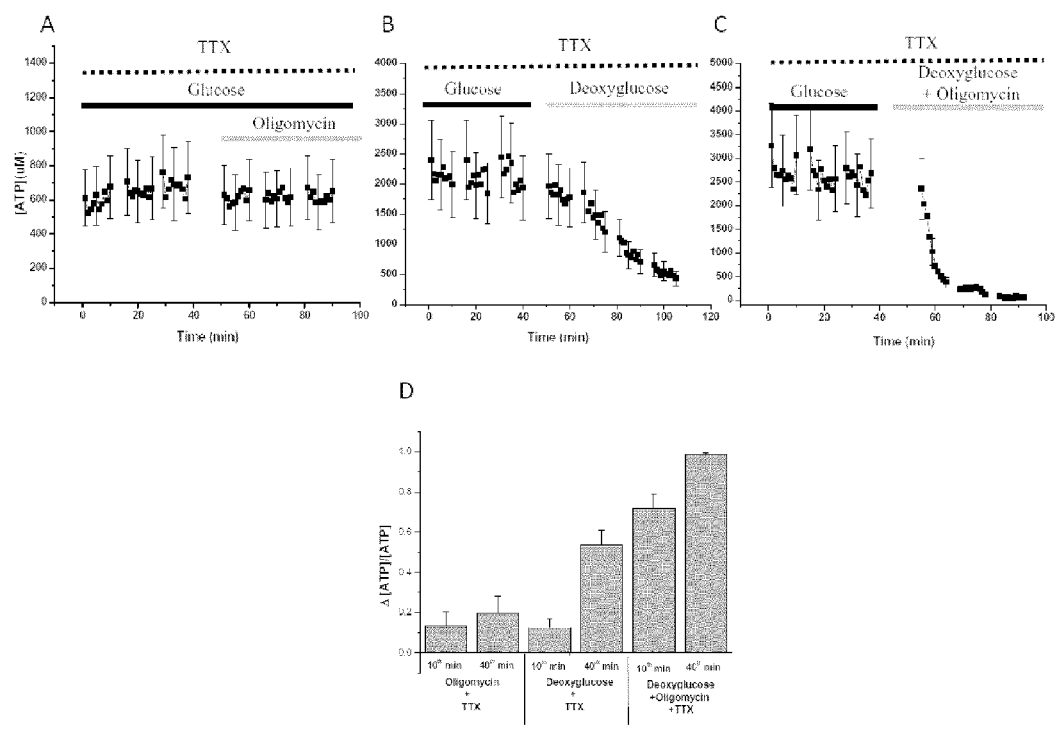
FIG. 15 is a representation of the regulation of [ATP] at rest that shows that ATP is primarily being supplied by the glycolytic pathway as [ATP] decreases upon blockade of glycolysis with 2-deoxyglucose (A). When challenged with an inhibitor of mitochondrial ATP synthase (oligomycin) [ATP] does not change (B). When [ATP] levels decrease however during inhibition of glycolysis, the cell beings to rely on mitochondrial function as the combined action of 2-deoxyglucose and oligomycin causes much more rapid decreases in [ATP] (C).

FIGS. 15A-15D show the use of Syn-ATP to determine the primary source of ATP in neurons under resting condition. FIG. 15A shows ATP measurements that were performed as in example 10 in nerve terminals expressing Syn-ATP. In the presence of TTX to block any action potential firing, neurons were treated with oligomycin, a potent inhibitor of the mitochondrial F0-F1 ATPase. This data shows that under these conditions mitochondria are not supplying ATP. In contrast, incubating neurons with a competitive inhibitor of glycolysis, deoxyglucose leads to a prompt decrease in ATP levels (see FIG. 15B). Thus for resting neurons the primary source of ATP is from glycolysis. During blockade of glycolysis however there is a synergistic relationship with ATP from mitochondria and blockade of both pathways leads to a much faster depletion of ATP (see FIG. 15C). A bar graph showing the effects of oligomycin and TTX, deoxyglucose and TTX and both deoxyglucose and deoxyglucose with TTX is presented in FIG. 15D.

Example 11

ATP Dynamics During Synaptic Activity

Figure 16:
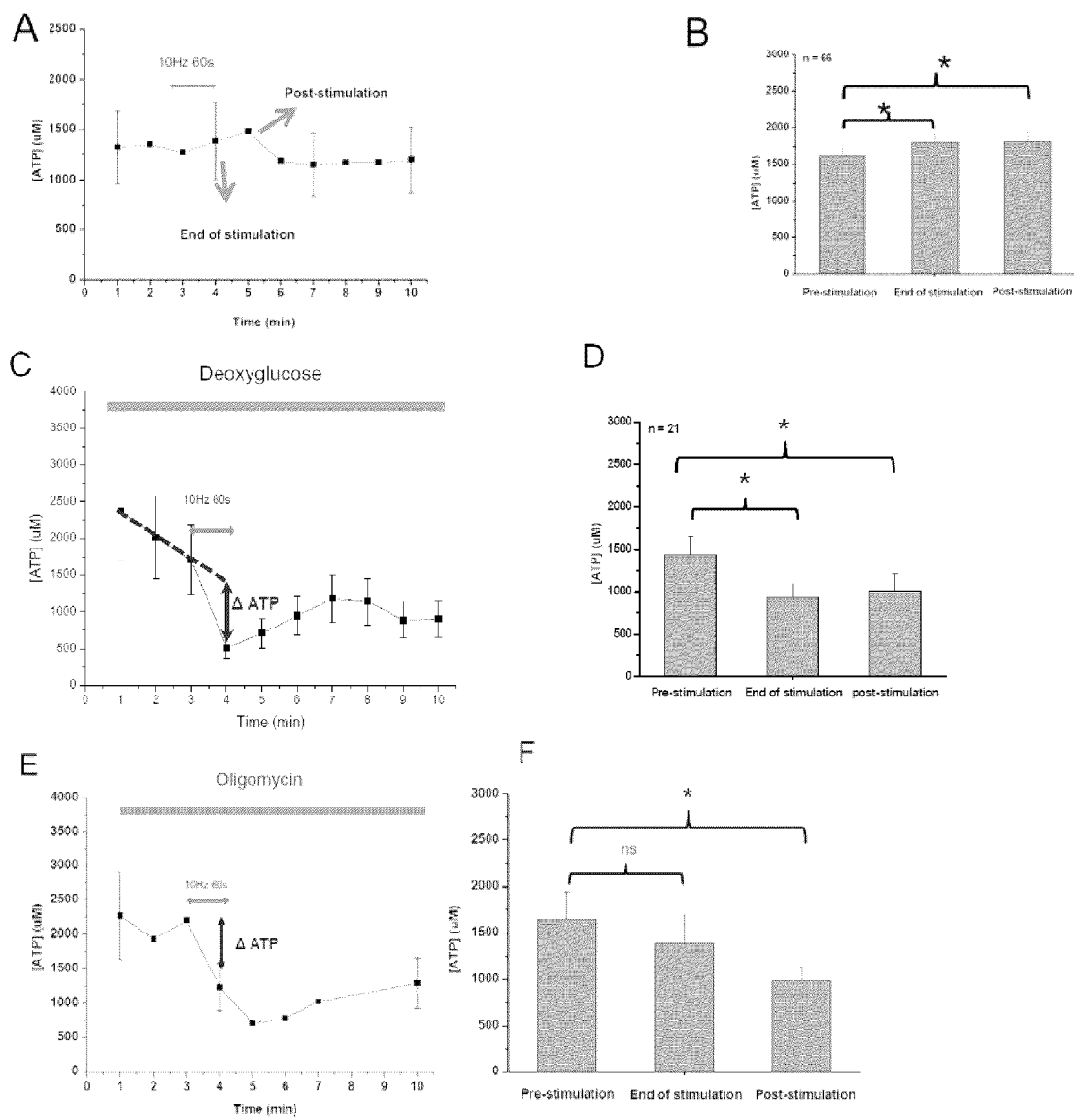
FIG. 16 is a representation of ATP dynamics during synaptic activity showing that even robust stimulation does not perturb [ATP] unless the ATP-synthesis pathways are perturbed. Both glycolysis and mitochondrial ATP synthesis are required to replenish [ATP] during synaptic activity.

FIG. 16A shows an example of the time course of intracellular ATP at nerve terminals reported by Syn-ATP before and after a 60 s period of 10 Hz action potential firing. Even during robust stimulation ATP levels are well maintained and show no depletion. FIG. 16B illustrates quantification from many cells showing only a small increase in the ATP levels in the period following activity. FIG. 16C shows an example of the time course of ATP levels when glycolysis and synapses are stimulated to fire action potentials. In this case activity lease to a depletion of ATP levels. FIG. 16D illustrates quantification over many neurons showing that at synapses ATP decrease by ~500 uM as a result of activity when glycolysis is blocked. FIG. 16E provides an example of the time course of ATP levels when mitochondrial ATP synthesis is blocked and synapses are stimulated to fire action potentials. In this case activity leads to a depletion of ATP levels. FIG. 16F illustrates quantification over many neurons showing that at synapses ATP decrease by ~250 uM as a result of activity when glycolysis is blocked but continues to decrease after this period.

Example 12

Figure 17:
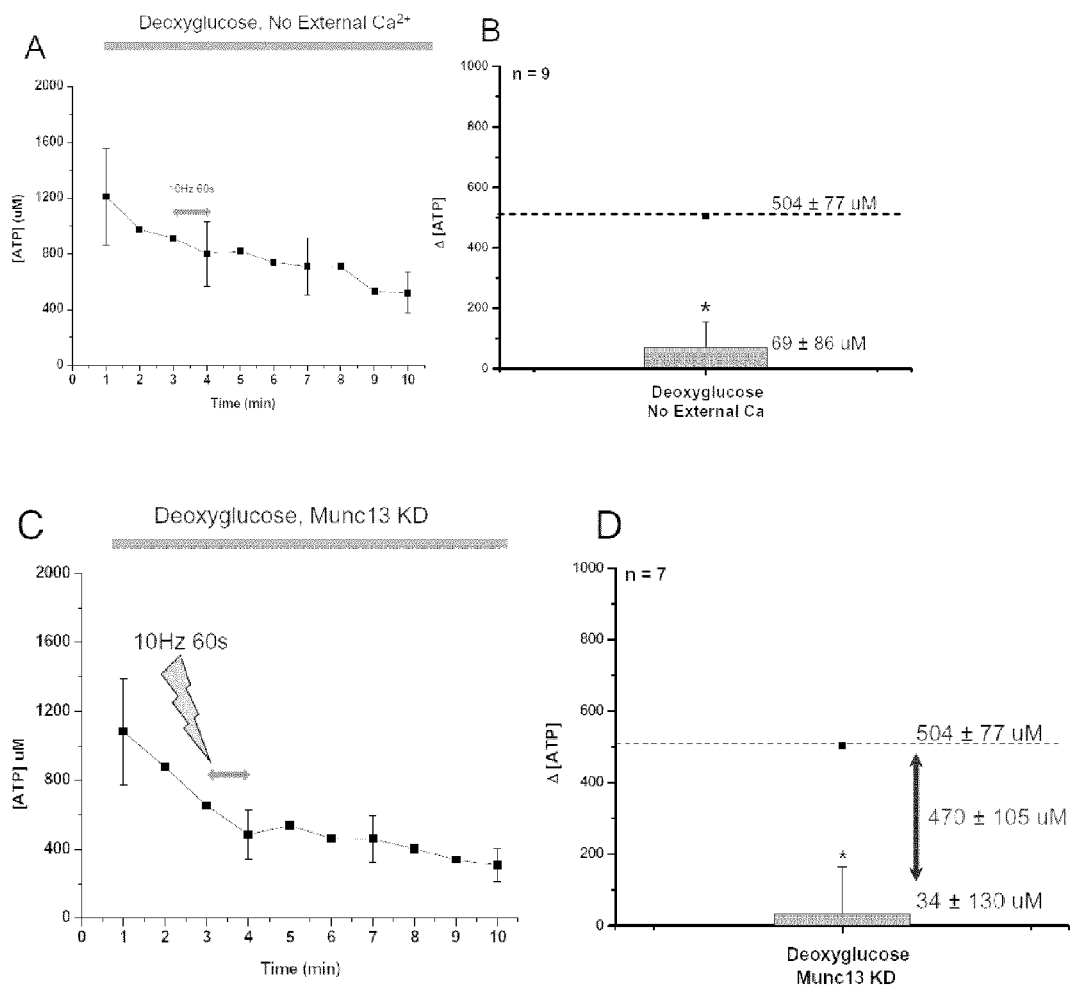
FIG. 17 illustrates that the primary consumers of ATP at synapses are steps associated with membrane traffic.

The Primary Consumers of ATP at Synapses are Steps Associated with Membrane Traffic FIG. 17A provides an example of the time course of ATP during stimulation with blockade of glycolysis but in the absence of external calcium. FIG. 17B illustrates quantification of many experiments performed as in FIG. 17A and shows that action potential firing alone (all calcium-dependent steps are now blocked) consumes much less ATP compared to control (i.e. with external calcium). FIG. 17C provides an example of the time course of ATP during stimulation in neurons that in which expression of munc-13, a protein necessary for exocytosis, has been suppressed. FIG. 17D illustrates quantification of many experiments as in FIG. 17C showing that stimulation in the absence of exocytosis is similar to removing external calcium. These experiments demonstrate that the primary demand on ATP supply at nerve terminals arises from exocytosis of synaptic vesicles.

REFERENCES

1. Fuji H. et al. Anal. Biochem. 366, 131 (2007)
2. Branchini B R. et al. Anal. Biochem. 361, 253 (2007)
3. Gajewski C. D. Mol. Biol. Cell 14, 3628 (2003)
4. Ryan T A. J. Neurosci 19:1317-1323 (1999)
5. Sankaranarayanan S & Ryan T. A. Nature Cell Biol. 2, 197-204 (2000)
6. Shepherd, G. M., and Harris, K. M. (1998) *J Neurosci* 18, 8300-8310
7. Pellerin, L., Pellegri, G., Bittar, P. G., Charnay, Y., Bouras, C., Martin, J. L., Stella, N., and Magistretti, P. J. (1998) *Dev Neurosci* 20, 291-299
8. Kang, J. S., Tian, J. H., Pan, P. Y., Zald, P., Li, C., Deng, C., and Sheng, Z. H. (2008) *Cell* 132, 137-148
9. Glater, E. E., Megeath, L. J., Stowers, R. S., and Schwarz, T. L. (2006) *J Cell Biol* 173, 545-557
10. Stowers, R. S., Megeath, L. J., Gorska-Andrzejak, J., Meinertzhagen, I. A., and Schwarz, T. L. (2002) *Neuron* 36, 1063-1077
11. Wang, X., and Schwarz, T. L. (2009) *Cell* 136, 163-174
12. Gajewski, C. D., Yang, L., Schon, E. A., and Manfredi, G. (2003) *Mol Biol Cell* 14, 3628-3635
13. Berg, J., Hung, Y. P., and Yellen, G. (2009) *Nat Methods* 6, 161-166
14. Chen, H., and Chan, D. C. (2006) *Curr Opin Cell Biol* 18, 453-459
15. Petrozzi, L., Ricci, G., Giglioli, N. J., Siciliano, G., and Mancuso, M. (2007) *Biosci Rep* 27, 87-104
16. Bell, C. J., Manfredi, G., Griffiths, E. J., and Rutter, G. A. (2007) *Methods Cell Biol* 80, 341-352
17. Coulon, V., Audet, M., Homburger, V., Bockaert, J., Fagni, L., Bouvier, M., and Perroy, J. (2008) *Biophys J* 94, 1001-1009
18. Balaji, J., and Ryan, T. A. (2007) *Proc Natl Acad Sci USA* 104, 20576-20581
19. Kim, S. H., and Ryan, T. A. (2009) *J Neurosci* 29, 3865-3874
20. Zhu, Y., Xu, J., and Heinemann, S. F. (2009) *Neuron* 61, 397-411
21. Tisi L. C, P. J. W., D. J. Squirrell, M. J. Murphy, C. R. Lowe, J. A. H. Murray. (2002) *Analytica Chimica Acta* 457, 115-123
22. Ryan, T. A., and Smith, S. J. (1995) *Neuron* 14, 983-989
23. Balaji, J., Armbruster, M., and Ryan, T. A. (2008) *J Neurosci* 28, 6742-6749

Nucleotide Sequences

```
                                                  SEQ ID NO: 1
Nucleic acid sequence of Photonis pyralis
luciferase
ATGGAAGACGCCAAAAACATAAAGAAAGGCCCGGCGCCATT

CTATCCGCTGGAAGATGGAACCGCTGGAGAGCAACTGCATAAGGCTATGA

AGAGATACGCCCTGGTTCCTGGAACAATTGCTTTTACAGATGCACATATC

GAGGTGGACATCACTTACGCTGAGTACTTCGAAATGTCCGTTCGGTTGGC

AGAAGCTATGAAACGATATGGGCTGAATACAAATCACAGAATCGTCGTAT

GCAGTGAAAACTCTCTTCAATTCTTTATGCCGGTGTTGGGCGCGTTATTT

ATCGGAGTTGCAGTTGCGCCCGCGAACGACATTTATAATGAACGTGAATT

GCTCAACAGTATGGGCATTTCGCAGCCTACCGTGGTGTTCGTTTCCAAAA

AGGGGTTGCAAAAAATTTTGAACGTGCAAAAAAAGCTCCCAATCATCCAA

AAAATTATTATCATGGATTCTAAAACGGATTACCAGGGATTTCAGTCGAT

GTACACGTTCGTCACATCTCATCTACCTCCCGGTTTTAATGAATACGATT

TTGTGCCAGAGTCCTTCGATAGGGACAAGACAATTGCACTGATCATGAAC

TCCTCTGGATCTACTGGTCTGCCTAAAGGTGTCGCTCTGCCTCATAGAAC

TGCCTGCGTGAGATTCTCGCATGCCAGAGATCCTATTTTTGGCAATCAAA

TCATTCCGGATACTGCGATTTTAAGTGTTGTTCCATTCCATCACGGTTTT

GGAATGTTTACTACACTCGGATATTTGATATGTGGATTTCGAGTCGTCTT

AATGTATAGATTTGAAGAAGAGCTGTTTCTGAGGAGCCTTCAGGATTACA

AGATTCAAAGTGCGCTGCTGGTGCCAACCCTATTCTCCTTCTTCGCCAAA

AGCACTCTGATTGACAAATACGATTTATCTAATTTACACGAAATTGCTTC

TGGTGGCGCTCCCCTCTCTAAGGAAGTCGGGGAAGCGGTTGCCAAGAGGT

TCCATCTGCCAGGTATCAGGCAAGGATATGGGCTCACTGAGACTACATCA

GCTATTCTGATTACACCCGAGGGGGATGATAAACCGGGCGCGGTCGGTAA

AGTTGTTCCATTTTTTGAAGCGAAGGTTGTGGATCTGGATACCGGGAAAA

CGCTGGGCGTTAATCAAAGAGGCGAACTGTGTGTGAGAGGTCCTATGATT

ATGTCCGGTTATGTAAACAATCCGGAAGCGACCAACGCCTTGATTGACAA

GGATGGATGGCTACATTCTGGAGACATAGCTTACTGGGACGAAGACGAAC

ACTTCTTCATCGTTGACCGCCTGAAGTCTCTGATTAAGTACAAAGGCTAT

CAGGTGGCTCCCGCTGAATTGGAATCCATCTTGCTCCAACACCCCAACAT

CTTCGACGCAGGTGTCGCAGGTCTTCCCGACGATGACGCCGGTGAACTTC

CCGCCGCCGTTGTTGTTTTGGAGCACGGAAAGACGATGACGGAAAAAGAG

ATCGTGGATTACGTCGCCAGTCAAGTAACAACCGCGAAAAAGTTGCGCGG

AGGAGTTGTGTTTGTGGACGAAGTACCGAAAGGTCTTACCGGAAAACTCG

ACGCAAGAAAAATCAGAGAGATCCTCATAAAGGCCAAGAAGGGCGGAAAG

ATCGCCGTGTAA

SEQ ID NO: 2
-- Nucleic acid sequence of mCherry:
ATGGTGAGCAAGGGCGAGGAGGATAACATGGCCATCATCAA

GGAGTTCATGCGCTTCAAGGTGCACATGGAGGGCTCCGTGAACGGCCACG

AGTTCGAGATCGAGGGCGAGGGCGAGGGCCGCCCCTACGAGGGCACCCA

GACCGCCAAGCTGAAGGTGACCAAGGGTGGCCCCCTGCCCTTCGCCTGGG

ACATCCTGTCCCCTCAGTTCATGTACGGCTCCAAGGCCTACGTGAAGCAC

CCCGCCGACATCCCCGACTACTTGAAGCTGTCCTTCCCCGAGGGCTTCAA

GTGGGAGCGCGTGATGAACTTCGAGGACGGCGGCGTGGTGACCGTGACCC

AGGACTCCTCCCTGCAGGACGGCGAGTTCATCTACAAGGTGAAGCTGCGC
```

-continued

GGCACCAACTTCCCCTCCGACGGCCCCGTAATGCAGAAGAAGACCATGGG

CTGGGAGGCCTCCTCCGAGCGGATGTACCCCGAGGACGGCGCCCTGAAGG

GCGAGATCAAGCAGAGGCTGAAGCTGAAGGACGGCGGCCACTACGACGCT

GAGGTCAAGACCACCTACAAGGCCAAGAAGCCCGTGCAGCTGCCCGGCG

CCTACAACGTCAACATCAAGTTGGACATCACCTCCCACAACGAGGACTAC

ACCATCGTGGAACAGTACGAACGCGCCGAGGGCCGCCACTCCACCGGCGG

CATGGACGAGCTGTACAAG

SEQ ID NO: 3
--Nucleic Acid Sequence of Synaptophysin:
ATGGACGTGGTGAATCAGCTGGTGGCTGGGGGTCAGTTCCG

GGTGGTCAAGGAGCCCCTTGGCTTCGTGAAGGTGCTGCAGTGGGTCTTTG

CCATCTTCGCCTTTGCTACGTGTGGCAGCTACACCGGGGAGCTTCGGCTG

AGCGTGGAGTGTGCCAACAAGACGGAGAGTGCCCTCAACATCGAAGTTGA

ATTCGAGTACCCCTTCAGGCTGCACCAAGTGTACTTTGATGCACCCTCCT

GCGTCAAAGGGGGCACTACCAAGATCTTCCTGGTTGGGGACTACTCCTCG

TCGGCTGAATTCTTTGTCACCGTGGCTGTGTTTGCCTTCCTCTACTCCAT

GGGGGCCCTGGCCACCTACATCTTCCTGCAGAACAAGTACCGAGAGAACA

ACAAAGGGCCTATGATGGACTTTCTGGCTACAGCCGTGTTCGCTTTCATG

TGGCTAGTTAGTTCATCAGCCTGGGCCAAAGGCCTGTCCGATGTGAAGAT

GGCCACGGACCCAGAGAACATTATCAAGGAGATGCCCATGTGCCGCCAGA

CAGGGAACACATGCAAGGAACTGAGGGACCCTGTGACTTCAGGACTCAAC

ACCTCAGTGGTGTTTGGCTTCCTGAACCTGGTGCTCTGGGTTGGCAACTT

ATGGTTCGTGTTCAAGGAGACAGGCTGGGCAGCCCCATTCATGCGCGCAC

CTCCAGGCGCCCCGGAAAAGCAACCAGCACCTGGCGATGCCTACGGCGAT

GCGGGCTACGGGCAGGGCCCCGGAGGCTATGGGCCCAAGACTCCTACGG

GCCTCAGGGTGGTTATCAACCCGATTACGGGCAGCCAGCCAGCGGTGGCG

GTGGCTACGGGCCTCAGGGCGACTATGGGCAGCAAGGCTATGGCCAACAG

GGTGCGCCCACCTCCTTCTCCAATCAGATG

SEQ ID NO: 4
Nucleic acid sequence of one form of Syn-ATP
encoding the gene for synaptophysin linked
to the gene for mCherry linked to the gene
for luciferase
. . . *GGAGACCCAAGCTTGGTACCGAGCT*__*GGATCC(BamHI)*__

*GCGGCCGCTCTAGGCTACCGGACTCAGATCTCGAGCTCAATCCTGAATTC*

*[ATGGACGTGGTGAATCAGCTGGTGGCTGGGGGTCAGTTCCGGGTGGTCA*

*AGGAGCCCCTTGGCTTCGTGAAGGTGCTGCAGTGGGTCTTTGCCATCTTC*

*GCCTTTGCTACGTGTGGCAGCTACACCGGGGAGCTTCGGCTGAGCGTGGA*

*GTGTGCCAACAAGACGGAGAGTGCCCTCAACATCGAAGTTGAATTCGAGT*

*ACCCCTTCAGGCTGCACCAAGTGTACTTTGATGCACCCTCCTGCGTCAAA*

*GGGGGCACTACCAAGATCTTCCTGGTTGGGGACTACTCCTCGTCGGCTGA*

*ATTCTTTGTCACCGTGGCTGTGTTTGCCTTCCTCTACTCCATGGGGGCCC*

*TGGCCACCTACATCTTCCTGCAGAACAAGTACCGAGAGAACAACAAAGGG*

*CCTATGATGGACTTTCTGGCTACAGCCGTGTTCGCTTTCATGTGGCTAGT*

-continued

*TAGTTCATCAGCCTGGGCCAAAGGCCTGTCCGATGTGAAGATGGCCACGG*

*ACCCAGAGAACATTATCAAGGAGATGCCCATGTGCCGCCAGACAGGGAAC*

*ACATGCAAGGAACTGAGGGACCCTGTGACTTCAGGACTCAACACCTCAGT*

*GGTGTTTGGCTTCCTGAACCTGGTGCTCTGGGTTGGCAACTTATGGTTCG*

*TGTTCAAGGAGACAGGCTGGGCAGCCCCATTCATGCGCGCACCTCCAGGC*

*GCCCCGGAAAAGCAACCAGCACCTGGCGATGCCTACGGCGATGCGGGCTA*

*CGGGCAGGGCCCCGGAGGCTATGGGCCCAAGACTCCTACGGGCCTCAGG*

*GTGGTTATCAACCCGATTACGGGCAGCCAGCCAGCGGTGGCGGTGGCTAC*

*GGGCCTCAGGGCGACTATGGGCAGCAAGGCTATGGCCAACAGGGTGCGCC*

*CACCTCCTTCTCCAATCAGATG*(synaptophysin)__*GGATCC*__

__*(BamHI)*__*ACTAGTAACGGCCGCCAGTGTGCTGGAATTCTGCA*__*GATATC*__

__*(EcoRV)*__*G[ATGGTGAGCAAGGGCGAGGAGGATAACATGGCCATCATCAA*

*GGAGTTCATGCGCTTCAAGGTGCACATGGAGGGCTCCGTGAACGGCCACG*

*AGTTCGAGATCGAGGGCGAGGGCGAGGGCCGCCCCTACGAGGGCACCCAG*

*ACCGCCAAGCTGAAGGTGACCAAGGGTGGCCCCCTGCCCTTCGCCTGGGA*

*CATCCTGTCCCCTCAGTTCATGTACGGCTCCAAGGCCTACGTGAAGCACC*

*CCGCCGACATCCCCGACTACTTGAAGCTGTCCTTCCCCGAGGGCTTCAAG*

*TGGGAGCGCGTGATGAACTTCGAGGACGGCGGCGTGGTGACCGTGACCCA*

*GGACTCCTCCCTGCAGGACGGCGAGTTCATCTACAAGGTGAAGCTGCGCG*

*GCACCAACTTCCCCTCCGACGGCCCCGTAATGCAGAAGAAGACCATGGGC*

*TGGGAGGCCTCCTCCGAGCGGATGTACCCCGAGGACGGCGCCCTGAAGGG*

*CGAGATCAAGCAGAGGCTGAAGCTGAAGGACGGCGGCCACTACGACGCTG*

*AGGTCAAGACCACCTACAAGGCCAAGAAGCCCGTGCAGCTGCCCGGCGCC*

*TACAACGTCAACATCAAGTTGGACATCACCTCCCACAACGAGGACTACAC*

*CATCGTGGAACAGTACGAACGCGCCGAGGGCCGCCACTCCACCGGCGGCA*

*TGGACGAGCTGTACAAG*(mCherry)]*GG*__*ACCGGT(AgeI)*__

*GCTAGCGGTACCGAGCTCGGATCCACTAGTCCAGTGTGGTGGAATTGCCC*

*TT[ATGGAAGACGCCAAAAACATAAAGAAAGGCCCGGCGCCATTCTATCC*

*GCTGGAAGATGGAACCGCTGGAGAGCAACTGCATAAGGCTATGAAGAGAT*

*ACGCCCTGGTTCCTGGAACAATTGCTTTTACAGATGCACATATCGAGGTG*

*GACATCACTTACGCTGAGTACTTCGAAATGTCCGTTCGGTTGGCAGAAGC*

*TATGAAACGATATGGGCTGAATACAAATCACAGAATCGTCGTATGCAGTG*

*AAAACTCTCTTCAATTCTTTATGCCGGTGTTGGGCGCGTTATTTATCGGA*

*GTTGCAGTTGCGCCCGCGAACGACATTTATAATGAACGTGAATTGCTCAA*

*CAGTATGGGCATTTCGCAGCCTACCGTGGTGTTCGTTTCCAAAAAGGGGT*

*TGCAAAAAATTTTGAACGTGCAAAAAAAGCTCCCAATCATCCAAAAAATT*

*ATTATCATGGATTCTAAAACGGATTACCAGGGATTTCAGTCGATGTACAC*

*GTTCGTCACATCTCATCTACCTCCCGGTTTTAATGAATACGATTTTGTGC*

*CAGAGTCCTTCGATAGGGACAAGACAATTGCACTGATCATGAACTCCTCT*

*GGATCTACTGGTCTGCCTAAAGGTGTCGCTCTGCCTCATAGAACTGCCTG*

*CGTGAGATTCTCGCATGCCAGAGATCCTATTTTTGGCAATCAAATCATTC*

-continued

```
CGGATACTGCGATTTTAAGTGTTGTTCCATTCCATCACGGTTTTGGAATG
TTTACTACACTCGGATATTTGATATGTGGATTTCGAGTCGTCTTAATGTA
TAGATTTGAAGAAGAGCTGTTTCTGAGGAGCCTTCAGGATTACAAGATTC
AAAGTGCGCTGCTGGTGCCAACCCTATTCTCCTTCTTCGCCAAAAGCACT
CTGATTGACAAATACGATTTATCTAATTTACACGAAATTGCTTCTGGTGG
CGCTCCCCTCTCTAAGGAAGTCGGGGAAGCGGTTGCCAAGAGGTTCCATC
TGCCAGGTATCAGGCAAGGATATGGCTCACTGAGACTACATCAGCTATT
CTGATTACACCCGAGGGGATGATAAACCGGGCGCGGTCGGTAAAGTTGT
TCCATTTTTTGAAGCGAAGGTTGTGGATCTGGATACCGGGAAAACGCTGG
GCGTTAATCAAAGAGGCGAACTGTGTGTGAGAGGTCCTATGATTATGTCC
GGTTATGTAAACAATCCGGAAGCGACCAACGCCTTGATTGACAAGGATGG
ATGGCTACATTCTGGAGACATAGCTTACTGGGACGAAGACGAACACTTCT
```

```
TCATCGTTGACCGCCTGAAGTCTCTGATTAAGTACAAAGGCTATCAGGTG
GCTCCCGCTGAATTGGAATCCATCTTGCTCCAACACCCCAACATCTTCGA
CGCAGGTGTCGCAGGTCTTCCCGACGATGACGCCGGTGAACTTCCCGCCG
CCGTTGTTGTTTTGGAGCACGGAAAGACGATGACGGAAAAAGAGATCGTG
GATTACGTCGCCAGTCAAGTAACAACCGCGAAAAAGTTGCGCGGAGGAGT
TGTGTTTGTGGACGAAGTACCGAAAGGTCTTACCGGAAAACTCGACGCAA
GAAAAATCAGAGAGATCCTCATAAAGGCCAAGAAGGGCGGAAAGATCGCC
GTGTAA(Luciferase)**GCGGCC(GC(NotI)** *TCGAG* . . .
```

For SEQ ID NO: 4, each gene is demarked by brackets [ ] and identified in parentheses following the gene sequence. The restriction sites are underlined and identified in boldface. The restriction enzyme that recognizes each site is identified in parentheses following the identified restriction site. Linking sequences are denoted in italics.

SEQ ID NO: 5

```
-- Syn-ATP amino acid sequence
M D V V N Q L V A G G Q F R V V K E P L G F V K V L Q W V F
A I F A F A T C G S Y T G E L R L S V E C A N K T E S A L N I E V E F
E Y P F R L H Q V Y F D A P S C V K G G T T K I F L V G D Y S S S A E
F F V T V A V F A F L Y S M G A L A T Y I F L Q N K Y R E N N K G P M
M D F L A T A V F A F M W L V S S S A W A K G L S D V K M A T D P E N
I I K E M P M C R Q T G N T C K E L R D P V T S G L N T S V V F G F L
N L V L W V G N L W F V F K E T G W A A P F M R A P P G A P E K Q P A
P G D A Y G D A G Y G Q G P G G Y G P Q D S Y G P Q G G Y Q P D Y G Q
P A S G G G G Y G P Q G D Y G Q Q G Y G Q Q G A P T S F S N Q M G S T
S N G R Q C A G I L Q I S M V S K G E E D N M A I I K E F M R F K V H
M E G S V N G H E F E I E G E G E G R P Y E G T Q T A K L K V T K G G
P L P F A W D I L S P Q F M Y G S K A Y V K H P A D I P D Y L K L S F
P E G F K W E R V M N F E D G G V V T V T Q D S S L Q D G E F I Y K V
K L R G T N F P S D G P V M Q K K T M G W E A S S E R M Y P E D G A L
K G E I K Q R L K L K D G G H Y D A E V K T T Y K A K K P V Q L P G A
Y N V N I K L D I T S H N E D Y T I V E Q Y E R A E G R H S T G G M D
E L Y K G P V L A M E D A K N I K K G P A P F Y P L E D G T A G E Q L
H K A M K R Y A L V P G T I A F T D A H I E V D I T Y A E Y F E M S V
R L A E A M K R Y G L N T N H R I V V C S E N S L Q F F M P V L G A L
F I G V A V A P A N D I Y N E R E L L N S M G I S Q P T V V F V S K K
G L Q K I L N V Q K K L P I I Q K I I I M D S K T D Y Q G F Q S M Y T
F V T S H L P P G F N E Y D F V P E S F D R D K T I A L I M N S S G S
T G L P K G V A L P H R T A C V R F S H A R D P I F G N Q I I P D T A
I L S V V P F H H G F G M F T T L G Y L I C G F R V V L M Y R F E E E
L F L R S L Q D Y K I Q S A L L V P T L F S F F A K S T L I D K Y D L
S N L H E I A S G G A P L S K E V G E A V A K R F H L P G I R Q G Y G
```

```
L T E T T S A I L I T P E G D D K P G A V G K V V P F F E A K V V D L
D T G K T L G V N Q R G E L C V R G P M I M S G Y V N N P E A T N A L
I D K D G W L H S G D I A Y W D E D E H F F I V D R L K S L I K Y K G
Y Q V A P A E L E S I L L Q H P N I F D A G V A G L P D D D A G E L P
A A V V V L E H G K T M T E K E I V D Y V A S Q V T T A K K L R G G V
V F V D E V P K G L T G K L D A R K I R E I L I K A K K G G K I A V
Stop
```

SEQ ID NO: 6

```
--- Syn-ATP* modified amino acid sequence
M D V V N Q L V A G G Q F R V V K E P L G F V K V L Q W V F
A I F A F A T C G S Y T G E L R L S V E C A N K T E S A L N I E V E F
E Y P F R L H Q V Y F D A P S C V K G G T T K I F L V G D Y S S S A E
F F V T V A V F A F L Y S M G A L A T Y I F L Q N K Y R E N N K G P M
M D F L A T A V F A F M W L V S S S A W A K G L S D V K M A T D P E N
I I K E M P M C R Q T G N T C K E L R D P V T S G L N T S V V F G F L
N L V L W V G N L W F V F K E T G W A A P F M R A P P G A P E K Q P A
P G D A Y G D A G Y G Q G P G G Y G P Q D S Y G P Q G G Y Q P D Y G Q
P A S G G G G Y G P Q G D Y G Q Q G Y G Q Q G A P T S F S N Q M G S T
S N G R Q C A G I L Q I S M V S K G E E D N M A I I K E F M R F K V H
M E G S V N G H E F E I E G E G E G R P Y E G T Q T A K L K V T K G G
P L P F A W D I L S P Q F M Y G S K A Y V K H P A D I P D Y K L S F
P E G F K W E R V M N F E D G G V V T V T Q D S S L Q D G E F I Y K V
K L R G T N F P S D G P V M Q K K T M G W E A S S E R M Y P E D G A L
K G E I K Q R L K L K D G G H Y D A E V K T T Y K A K K P V Q L P G A
Y N V N I K L D I T S H N E D Y T I V E Q Y E R A E G R H S T G G M D
E L Y K G P V L A M E D A K N I K K G P A P F Y P L E D G T A G E Q L
H K A M K R Y A L V P G T I A F T D A H I E V N I T Y A E Y F E M S V
R L A E A M K R Y G L N T N H R I V V C S E N S L Q F F M P V L G A L
F I G V A V A P A N D I Y N E R E L L N S M N I S Q P T V V F V S K K
G L Q K I L N V Q K K L P I I Q K I I I M D S K T D Y Q G F Q S M Y T
F V T S H L P P G F N E Y D F V P E S F D R D K T I A L I M N S S G S
T G L P K G V A L P H R A L C V R F S H A R D P I F G N Q I A P D T A
I L S V V P F H H G F G M F T T L G Y L I C G F R V V L M Y R F E E E
L F L R S L Q D Y K I Q S A L L V P T L F S F L A K S T L I D K Y D L
S N L H E I A S G G A P L S K E V G E A V A K R F H L P G I R Q G Y G
L T E T T S A I L I T P K G D D K P G A V G K V V P F F E A K V V D L
D T G K T L G V N Q R G E L C V R G P M I M S G Y V N N P E A T N A L
I D K D G W L H S G D L A Y W D E D E H F F I V G R L K S L I K Y K G
Y Q V A P A E L E S I L L Q H P N I F D A G V A G L P D D D A G E L P
A A V V V L E H G K T M T E K E I V D Y V A S Q V T T A K K L R G G V
V F V D E V P K G L T G K L D A R K I R E I L I K A K K G G K I A V
Stop
```

SEQ ID NO: 7

-- Syn-ATP* modified nucleotide sequence (underline: Synaptophysin, standard font: mCherry, italics: luciferase)

<u>ATGGACGTGGTGAATCAGCTGGTGGCTGGGGGTCAGTTCCG</u>

<u>GGTGGTCAAGGAGCCCCTTGGCTTCGTGAAGGTGCTGCAGTGGGTCTTTG</u>

<u>CCATCTTCGCCTTTGCTACGTGTGGCAGCTACACCGGGGAGCTTCGGCTGA</u>

<u>GCGTGGAGTGTGCCAACAAGACGGAGAGTGCCCTCAACATCGAAGTTGAA</u>

<u>TTCGAGTACCCCTTCAGGCTGCACCAAGTGTACTTTGATGCACCCTCCTGC</u>

<u>GTCAAAGGGGCACTACCAAGATCTTCCTGGTTGGGGACTACTCCTCGTC</u>

<u>GGCTGAATTCTTTGTCACCGTGGCTGTGTTTGCCTTCCTCTACTCCATGGG</u>

<u>GGCCCTGGCCACCTACATCTTCCTGCAGAACAAGTACCGAGAGAACAACA</u>

<u>AAGGGCCTATGATGGACTTTCTGGCTACAGCCGTGTTCGCTTTCATGTGGC</u>

<u>TAGTTAGTTCATCAGCCTGGGCCAAAGGCCTGTCCGATGTGAAGATGGCC</u>

<u>ACGGACCCAGAGAACATTATCAAGGAGATGCCCATGTGCCGCCAGACAG</u>

<u>GGAACACATGCAAGGAACTGAGGGACCCTGTGACTTCAGGACTCAACACC</u>

<u>TCAGTGGTGTTTGGCTTCCTGAACCTGGTGCTCTGGGTTGGCAACTTATGG</u>

<u>TTCGTGTTCAAGGAGACAGGCTGGGCAGCCCCATTCATGCGCGCACCTCC</u>

<u>AGGCGCCCCGGAAAAGCAACCAGCACCTGGCGATGCCTACGGCGATGCG</u>

<u>GGCTACGGGCAGGGCCCCGGAGGCTATGGGCCCCAAGACTCCTACGGGCC</u>

<u>TCAGGGTGGTTATCAACCCGATTACGGGCAGCCAGCCAGCGGTGGCGGTG</u>

<u>GCTACGGGCCTCAGGGCGACTATGGGCAGCAAGGCTATGGCCAACAGGGT</u>

<u>GCGCCCACCTCCTTCTCCAATCAGATGGGATCCACTAGTAACGGCCGCCA</u>

GTGTGCTGGAATTCTGCAGATATCGATGGTGAGCAAGGGCGAGGAGGATA

ACATGGCCATCATCAAGGAGTTCATGCGCTTCAAGGTGCACATGGAGGGC

TCCGTGAACGGCCACGAGTTCGAGATCGAGGGCGAGGGCGAGGGCCGCC

CCTACGAGGGCACCCAGACCGCCAAGCTGAAGGTGACCAAGGGTGGCCC

CCTGCCCTTCGCCTGGGACATCCTGTCCCCTCAGTTCATGTACGGCTCCAA

GGCCTACGTGAAGCACCCCGCCGACATCCCCGACTACTTGAAGCTGTCCTT

CCCCGAGGGCTTCAAGTGGGAGCGCGTGATGAACTTCGAGGACGGCGGCG

TGGTGACCGTGACCCAGGACTCCTCCCTGCAGGACGGCGAGTTCATCTAC

AAGGTGAAGCTGCGCGGCACCAACTTCCCCTCCGACGGCCCCGTAATGCA

GAAGAAGACCATGGGCTGGGAGGCCTCCTCCGAGCGGATGTACCCCGAG

GACGGCGCCCTGAAGGGCGAGATCAAGCAGAGGCTGAAGCTGAAGGACG

GCGGCCACTACGACGCTGAGGTCAAGACCACCTACAAGGCCAAGAAGCC

CGTGCAGCTGCCCGGCGCCTACAACGTCAACATCAAGTTGGACATCACCT

CCCACAACGAGGACTACACCATCGTGGAACAGTACGAACGCGCCGAGGG

CCGCCACTCCACCGGCGGCATGGACGAGCTGTACAAGGGACCGGTGCTAG

*CGATGGAAGACGCCAAAAACATAAAGAAAGGCCCGGCGCCATTCTATCCTCTA*

*GAGGATGGAACCGCTGGAGAGCAACTGCATAAGGCTATGAAGAGATACGCCCT*

*GGTTCCTGGAACAATTGCTTTTACAGATGCACATATCGAGGTGAACATCACGTA*

*CGCGGAATACTTCGAAATGTCCGTTCGGTTGGCAGAAGCTATGAAACGATATGG*

*GCTGAATACAAATCACAGAATCGTCGTATGCAGTGAAAACTCTCTTCAATTCTTT*

-continued

```
ATGCCGGTGTTGGGCGCGTTATTTATCGGAGTTGCAGTTGCGCCCGCGAACGA

CATTTATAATGAACGTGAATTGCTCAACAGTATGAACATTTCGCAGCCTACCGTA

GTGTTTGTTTCCAAAAAGGGGTTGCAAAAAATTTTGAACGTGCAAAAAAAATTAC

CAATAATCCAGAAAATTATTATCATGGATTCTAAAACGGATTACCAGGGATTTCA

GTCGATGTACACGTTCGTCACATCTCATCTACCTCCCGGTTTTAATGAATACGAT

TTTGTACCAGAGTCCTTTGATCGTGACAAAACAATTGCACTGATAATGAATTCCT

CTGGATCTACTGGGTTACCTAAGGGTGTGGCCCTTCCGCATAGAgCTctCTGCG

TCAGATTCTCGCAcGCCAGAGATCCAATaTTTGGCAATCAAATCgCTCCGGATAC

TGCGATTTTAAGTGTTGTTCCATTCCATCACGGTTTTGGAATGTTTACTACACTC

GGATATTTGATATGTGGATTTCGAGTCGTCTTAATGTATAGATTTGAAGAAGAGC

TGTTTTTACGATCCCTTCAGGATTACAAAATTCAAAGTGCGTTGCTAGTACCAAC

CCTATTTTCATTCTTgGCCAAAAGtACTCTGATTGACAAATACGATTTATCTAATTT

ACACGAAATTGCTTCTGGGGGCGCACCTCTTTCGAAAGAAGTCGGGGAAGCGG

TTGCAAAACGCTTCCATCTTCCAGGGATACGACAAGGATATGGGCTCACTGAGA

CTACTAGTGCTATTCTGATTACACCCaAGGGGGATGATAAACCGGGCGCGGTC

GGTAAAGTTGTTCCATTTTTTGAAGCGAAGGTTGTGGATCTGGATACCGGGAAA

ACGCTGGGCGTTAATCAGAGAGGCGAATTATGTGTCAGAGGACCTATGATTATG

TCCGGTTATGTAAACAATCCGGAAGCGACCAACGCCTTGATTGACAAGGATGGA

TGGCTACATTCTGGAGACCTAGCTTACTGGGACGAAGACGAACACTTCTTCATA

GTTGGCCGCTTGAAGTCTTTAATTAAATACAAAGGATATCAGGTGGCCCCCGCT

GAATTGGAATCGATATTGTTACAACACCCCAACATCTTCGACGCGGGCGTGGCA

GGTCTTCCCGACGATGACGCCGGTGAACTTCCCGCCGCCGTTGTTGTTTTGGA

GCACGGAAAGACGATGACGGAAAAAGAGATCGTGGATTACGTCGCCAGTCAAG

TAACAACCGCGAAAAGTTGCGCGGAGGAGTTGTGTTTGTGGACGAAGTACCG

AAAGGTCTTACCGGAAAACTCGACGCAAGAAAAATCAGAGAGATCCTCATAAAG

GCCAAGAAGGGCGGAAAGATCGCCGTGTAA
```

The invention claimed is:

1. A polynucleotide comprising a sequence that encodes an optical reporter construct for quantitative determining of ATP levels at a target site or local region, comprising a first region that encodes a luciferase, a second region that encodes a reporter fluorescent protein and third region that encodes a synaptophysin, wherein the first region, the second region and the third region are linked together in a single reading frame.

2. The polynucleotide of claim 1, wherein the first region encodes the luciferase from the North American firefly *Photonis pyralis* and has the sequence of SEQ ID No. 1.

3. The polynucleotide of claim 1, wherein the first region comprises a mutant of the luciferase gene from the North American firefly *Photonis pyralis*, SEQ ID No. 1, wherein the mutant encodes a luciferase with at least one of the following mutations: Thr214Ala, Ala215Leu, Ile232Ala, Phe295Leu, and Glu354Lys.

4. The polynucleotide of claim 1, wherein the first region comprises a mutant of the luciferase gene from the North American firefly *Photonis pyralis*, SEQ ID No. 1, wherein the mutant encodes a luciferase with a mutation selected from Ile423Leu, D436G, or both Ile423Leu and D436G.

5. The polynucleotide of claim 1 wherein the luciferase gene is present one or more times.

6. The polynucleotide of claim 1, wherein the second region comprises a gene that encodes GFP, mPlum, mCherry, tdTomato, mStrawberry, J-Red, DsRed-monomer, mOrange, mKO, mCitrine, Venus, YPet, EYFP, Emerald, EGFP, CyPet, mCFPm, Cerulean, or T-Sapphire.

7. The polynucleotide of claim 1, wherein the second region comprises SEQ ID NO: 2 and encodes mCherry.

8. The polynucleotide of claim 1, wherein the third region comprises SEQ ID NO: 3 and encodes synaptophysin.

9. A polynucleotide comprising a sequence that encodes a hybrid protein, wherein the sequence comprises a first region that encodes a reporter enzyme, a second region that encodes a reporter fluorescent protein and third region that encodes a targeting protein, wherein the first region, the second region and the third region are linked together in a single reading frame which comprises SEQ ID NO: 4 or SEQ ID NO: 7.

10. A polynucleotide comprising a sequence that encodes an optical reporter construct for determining local levels of ATP at synapses comprising a first region that encodes a reporter enzyme luciferase, a second region that encodes a reporter fluorescent protein, and a third region that encodes a protein for targeting to a synaptic vesicle selected from the group consisting of SV2, synapsin I, synapsin II, synaptotagmin (p65), vesicle associated membrane protein (synaptobrevin, VAMP), rab3A, VAT-1, vacuolar protein pump, high MW proteoglycan, synaptophysin, and combinations thereof, wherein the first region, the second region and the third region are linked together in a single reading frame.

11. The polynucleotide of claim 10, wherein the first region encodes the luciferase from the North American firefly *Photonis pyralis* and has the sequence of SEQ ID No. 1.

12. The polynucleotide of claim 10, wherein the first region comprises a mutant of the luciferase gene from the North American firefly *Photonis pyralis*, SEQ ID No. 1, wherein the mutant encodes a luciferase with at least one of the following mutations: Thr214Ala, Ala215Leu, Ile232Ala, Phe295Leu, and Glu354Lys.

13. The polynucleotide of claim 10, wherein the first region comprises a mutant of the luciferase gene from the North American firefly *Photonis pyralis*, SEQ ID No. 1, wherein the mutant encodes a luciferase with a mutation selected from Ile423Leu, D436G, or both Ile423Leu and D436G.

14. The isolated polynucleotide of claim 10, wherein the luciferase gene is present one or more times.

15. The polynucleotide of claim 10, wherein the second region comprises a gene that encodes GFP, mPlum, mCherry, tdTomato, mStrawberry, J-Red, DsRed-monomer, mOrange, mKO, mCitrine, Venus, YPet, EYFP, Emerald, EGFP, CyPet, mCFPm, Cerulean, and T-Sapphire.

16. The polynucleotide of claim 10, wherein the second region comprises SEQ ID NO: 2 and encodes mCherry.

17. The polynucleotide of claim 10, wherein the third region comprises SEQ ID NO: 3 and encodes synaptophysin.

* * * * *